US012779131B2

(12) United States Patent
Scheurer et al.

(10) Patent No.: US 12,779,131 B2
(45) Date of Patent: Nov. 3, 2026

(54) MODULAR INJECTION SYSTEM

(71) Applicant: Ypsomed AG, Burgdorf (CH)

(72) Inventors: Simon Scheurer, Bern (CH); Christian Schrul, Burgdorf (CH); Simon Martin Bosshard, Hindelbank (CH); Martin Bruegger, Bolligen (CH); Andreas Schneider, Basel (CH)

(73) Assignee: Ypsomed AG, Burgdorf (CH)

( * ) Notice: Subject to any disclaimer, the term of this patent is extended or adjusted under 35 U.S.C. 154(b) by 716 days.

(21) Appl. No.: 18/339,428

(22) Filed: Jun. 22, 2023

(65) Prior Publication Data

US 2023/0330349 A1 Oct. 19, 2023

Related U.S. Application Data

(63) Continuation of application No. PCT/EP2021/084696, filed on Dec. 8, 2021.

(30) Foreign Application Priority Data

Dec. 22, 2020 (EP) .................................... 20216386

(51) Int. Cl.
*A61M 5/315* (2006.01)
*A61M 5/20* (2006.01)
*A61M 5/24* (2006.01)
*A61M 5/31* (2006.01)

(52) U.S. Cl.
CPC .......... *A61M 5/31595* (2013.01); *A61M 5/20* (2013.01); *A61M 5/2425* (2013.01);
(Continued)

(58) Field of Classification Search
CPC .. A61M 5/31595; A61M 5/20; A61M 5/2425; A61M 5/3146; A61M 5/3158;
(Continued)

(56) References Cited

U.S. PATENT DOCUMENTS 4,968,299 A * 11/1990 Ahlstrand ........... A61M 5/2448
D24/114
2010/0292651 A1* 11/2010 Yodfat ................ A61M 5/1454
604/218
(Continued)

FOREIGN PATENT DOCUMENTS

EP 3669911 A1 6/2020
EP 3797811 A1 3/2021
(Continued)

OTHER PUBLICATIONS

Extended European Search Report issued in European Patent Application No. 20216386.1 mailed on Sep. 15, 2021, 9 pages.
(Continued)

*Primary Examiner* — James D Ponton
(74) *Attorney, Agent, or Firm* — Dorsey & Whitney LLP

(57) ABSTRACT

The present disclosure relates to a modular injection system including a first injection device including a first reservoir unit comprising a reservoir filled with medication, a housing for holding the reservoir and a plunger rod adapted to advance a piston inside the reservoir to dispense the medication and first automatic drive unit releasably attachable to the reservoir unit and including an automatic drive member automatically driven by a power source and adapted to be releasably coupled to the plunger rod. The modular system further comprises a second injection device including a second reservoir unit and a manual drive unit connected to the reservoir unit and including a manual drive member manually driven and connected to a plunger rod of the second reservoir unit. The first and second reservoir unit are identical.

18 Claims, 14 Drawing Sheets

(52) U.S. Cl.
CPC ........ *A61M 5/3146* (2013.01); *A61M 5/3158* (2013.01); *A61M 2005/2006* (2013.01); *A61M 2005/31588* (2013.01); *A61M 2205/6081* (2013.01)

(58) Field of Classification Search
CPC ........... A61M 2005/2006; A61M 2005/31588; A61M 2205/6081; A61M 5/24; A61M 2205/60; A61M 5/1413; A61M 2005/2026; A61M 5/2033; A61M 2005/14268; A61M 2005/3139
See application file for complete search history.

(56) References Cited

U.S. PATENT DOCUMENTS

| | | | | |
|---|---|---|---|---|
| 2011/0166512 | A1* | 7/2011 | Both | A61M 5/14248 604/152 |
| 2013/0274655 | A1* | 10/2013 | Jennings | A61M 5/3213 604/152 |
| 2021/0077735 | A1* | 3/2021 | Toporek | A61M 5/3155 |

FOREIGN PATENT DOCUMENTS

| | | | |
|---|---|---|---|
| EP | 4019064 | A1 | 6/2022 |
| WO | 2009092084 | A1 | 7/2009 |
| WO | 2012160156 | A2 | 11/2012 |
| WO | 2019112886 | A1 | 6/2019 |
| WO | 2019121616 | A1 | 6/2019 |
| WO | 2019122946 | A1 | 6/2019 |
| WO | 2019158372 | A1 | 8/2019 |
| WO | 2022135921 | A1 | 6/2022 |

OTHER PUBLICATIONS

International Search Report and Written Opinion issued in International Application No. PCT/EP2021/084696, mailed on May 23, 2022, 16 pages.

* cited by examiner

MODULAR INJECTION SYSTEM

CROSS-REFERENCE TO RELATED APPLICATIONS

This application claims priority to International Patent Application No. PCT/EP2021/084696 filed on Aug. 12, 2021, entitled "MODULAR INJECTION SYSTEM", which in turn claims priority to European Patent Application No. 20216386.1 filed on Dec. 22, 2020, entitled "MODULAR INJECTION SYSTEM", each of which is incorporated by reference herein, in the entirety and for all purposes.

TECHNICAL FIELD

The disclosure relates to injection devices or medicament delivery devices for injecting, delivering, administering, infusing or dispensing substances and/or liquids such as insulin, hormone preparations or vaccines. It departs from a modular injection system including an injection device including a reservoir unit and an automatic drive unit releasably attachable to the reservoir unit. The modular injection system further comprises a second injection device including an identical reservoir unit and a manual drive unit.

BACKGROUND

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time.

By way of example, diabetes may be treated by self-administration of insulin or its derivatives with the help of multi-variable-dose insulin injection pens. An injection pen device generally has an elongate device body defining a longitudinal main device axis. An automatic injection device has a motor or a drive spring for biasing a plunger rod and shifting a piston in a container barrel, where the drive spring may have to be charged or strained manually prior to injection of a dose. A manually powered delivery drive requires a user to manually provide the energy to move the piston, for instance by applying a distal force component to the injection device.

The medicament dose to be injected may typically be manually selected by turning a dosage knob and observing the actual dialed dose from a dose window or display of the insulin pen. A dose is dispensed by inserting the needle into a suited portion of human skin and by moving the piston manually or by pressing a release button of an automatic injection device.

There are several types of injection devices known in the art. Disposable injection devices are adapted to deliver medication from a container such as a pre-filled cartridge or syringe that is not intended to be replaced or refilled by the patient. Reusable, semi-disposable, or hybrid delivery devices have a components of the device that may be replaced by the patient, or a cartridge that may be refilled, while some components of the device may be reused with the replaced or refilled drug container.

WO 2019/112886 A1 discloses a delivery device comprising a disposable cassette having a cartridge housing and a reusable module having a main housing. A drive ribbon is disposed within cartridge housing and the cartridge holding a medication is mounted on the cartridge housing of the disposable cassette. A drive member mechanism of the drive ribbon is disposed in the main housing of the reusable module.

WO 2019/122946 A1 discloses an automatic injector device that comprises a single-use, disposable, drug delivery assembly and a reusable motorized transmission assembly. The disposable drug delivery assembly comprises a housing and a syringe, a plunger, a pre-filled unit-dose drug containing chamber and a needle. The reusable transmission assembly comprises a drive motor, a rechargeable battery, a control system and a screw threaded piston. After an injection the drug delivery assembly can be detached from the transmission assembly and disposed of in an appropriate manner whilst the drive transmission assembly can be re-used after reconnecting with a new, unused, drug delivery assembly.

WO 2019/158372 A1 discloses delivery device with a back-end reusable power pack unit and a front-end disposable drug cassette unit. The drug cassette unit is axially inserted into the reusable unit and being fixed by snap-connection due to expanding of a flexible parts. A medicament container is spaced within a housing of the disposable unit. A drive unit provided with a transmission and a battery is mounted on a frame adjacent to a closed end of the reusable unit. The medicament container is a syringe or a cartridge for a single or multiple delivery.

SUMMARY

It is an objective of the invention to allow a cost-effective manufacture, storing, and final assembly of different types of injection devices, in particular of disposable and semi-disposable injection devices.

This objective is achieved by a modular injection system according to the independent claims. Preferred embodiments are evident from the dependent claims.

The present disclosure relates to a modular injection system or an injection device family including more than one complete and fully functional injection device. The modular system comprises at least a first injection device, it may be a semi-disposable device, including

- a first reservoir unit including a reservoir filled with medication, a housing for non-removable holding the reservoir inside the housing and a plunger rod adapted to advance a piston inside the reservoir to dispense the medication;
- a first automatic drive unit releasably and directly or indirectly (via additional member) attachable to the reservoir unit and including an automatic drive member automatically driven by a power source and adapted to be coupled releasably and directly or indirectly (via additional member) to the plunger rod such that in an attached state an driving movement of the automatic drive member is converted into an advancing movement of the plunger rod, and a second injection device, it may be a fully disposable (one-way or single use) injection device, including

- a second reservoir unit;
- a manual drive unit, it may be non-releasably or non-dissociable, connected to the reservoir unit and including a manual drive member manually driven and directly or indirectly connected to a plunger rod of the second reservoir unit, where the first and second reservoir unit are identical and could be exchanged prior to final assembly of the two injection devices.

The injection system according to the disclosure is modular. Modular means that identical parts, components or sub-assemblies can be used for different variants of injection devices. This modularity allows a cost-efficient production, handling and final assembly of the different types of injection devices because the number of manufacturing tools, storage bins, or assembly installations can be reduced. There are less injection molding tools required because different types of injection devices comprise identical parts, components or sub-assemblies. At the same time the number of parts produced by one specific tool or machine is higher and thus the investment costs can be better distributed.

According to the present disclosure the first and second reservoir unit are identical. In other words, the first injection device and the second injection device differ in the drive unit but they have both the same type of reservoir unit.

The term "injection device" or "injector" refers to a device that is removed from the injection site after each medication event or drug delivery process. By contrast, an "infusion device" refers to a device with a cannula or needle that remains in the skin of the patient for a prolonged period of time, for example, several hours.

The injection device may be a pen-shaped injection device. In a preferred embodiment the first injection device may be a reusable, semi-reusable or semi-disposable injection device. A semi-disposable injection device comprises parts, components or a sub-assemblies that is disposed of (disposable part) after an injection or if the medication is fully dispensed. Additionally, it comprises further parts, components or a sub-assemblies that can be reused (reusable part) for several injections and successively with several disposable parts.

The reservoir unit may be replaced after one or more injections or after the medication of the reservoir is fully dispensed. The reservoir unit may be a disposable unit. In contrast, the drive unit may be used for several injections and for different reservoir units and forms or is part of a so-called reusable unit.

According to a first aspect the reservoir unit includes the plunger rod. If the reservoir unit is designed as a disposable unit the plunger rod is thus disposed with the reservoir. This is advantageous because the user does not have to reset or move the plunger rod when attaching a new reservoir unit to the automatic drive unit. Furthermore, the flange or tip of the plunger rod having contact with the reservoir does not have to be cleaned or otherwise prepared for a new injection as each new reservoir unit has its own new plunger rod and flange. Furthermore, the constant or non-releasable connection between the plunger rod and the flange acts as a single use protection, because the flange is not displaceable in axial direction without driving the plunger rod, where the plunger rot is not drivable without the drive unit. Thus, a refill of the reservoir unit by the user can be prevented.

The reservoir can be a container, cartridge, vial or ampule adapted to contain medication which can be dispensed out of the reservoir by a separate plunger rod or piston rod which is not part of the reservoir itself (but is part of the reservoir unit). The reservoir may be a cartridge, in particular a non-refillable cartridge for single use. A cartridge does not integrally comprise any plunger rod or piston rod.

The reservoir unit is not limited to pre-assembled parts. The reservoir unit may comprise a set of parts that are not hold together but constitute a set of single components. The reservoir unit may further comprise a holder engaging the plunger rod and positioning the plunger rod relative to the reservoir. This is advantageous if the cartridge is initially not completely filled and thus the plunger rod can be positioned accordingly.

The automatic drive unit is releasably or non-permanent attachable to the reservoir unit (or vice versa). The user can replace the reservoir unit if the reservoir is empty or has to be replaced or if the user intends to change the medication. The term "attachable" includes embodiments where the automatic drive unit is indirectly coupled to the reservoir unit by further parts, components or sub-assemblies in between. The automatic drive unit may be attached to the reservoir unit by an intermediate member such that the intermediate member is arranged in-between, and in turn attaches individually to both the reservoir unit and the automatic drive unit. And excluding a direct or immediate fit between the reservoir and drive unit. Alternatively, the automatic drive unit is directly coupled to the reservoir unit without any parts or components in between.

In terms of the modular concept proposed, the optional intermediate member may be signed to the drive unit, as it is not common, yet reusable.

As mentioned above the reservoir unit may be disposable. The reservoir unit may form the disposable part (disposable assembly) of the injection device or the reservoir unit may only constitute a part or a sub-assembly of the whole disposable assembly. The latter case means the disposable assembly may include further parts, units or sub-assemblies.

Automatic Drive Unit and Power Source

The automatic drive unit includes an automatic drive member which can be realized, for example, as a drive shaft or drive sleeve, as a motor with a motor shaft or as rotating or axially movable actuation element. The automatic drive member is adapted to be operatively and releasably coupled to the plunger rod when the automatic drive unit is attached to the reservoir unit. The term "coupled" includes embodiments with one or more intermediate parts, components or sub-assemblies between the automatic drive member and the plunger rod. If the automatic drive unit is directly or indirectly attached to the reservoir unit the automatic drive member is directly or indirectly via one or more intermediate parts, components or sub-assemblies coupled to the plunger rod. That means an advancing movement of the automatic drive member is converted into an advancing movement of the plunger rod. The movement can be a rotation, an axial shifting, a screw movement or a combination thereof.

The automatic drive member is driven by a power source such as, for example, a mechanical spring, an electric or an electromechanical power source, a single use or rechargeable electric battery, a hydraulic drive, a gas carpule or an electroactive polymer actuator (EAP) as disclosed in Patent Application EP 19199736.0.

As mentioned above the automatic drive unit may be reusable. The unit can be used for a plurality of successive injections with reservoir units. The drive unit may form the reusable part (reusable assembly) of the injection device or the drive unit may only constitute a part or a sub-assembly of the whole reusable assembly. That means the reusable assembly may include further parts, units or sub-assemblies.

Alternatively, the automatic drive unit and/or the manual drive unit is designed to be reused for several injections. In this case, the reservoir holder has to be releasably attachable to the rest of the device, such that the user is able to exchange or replace the reservoir (e.g. a cartridge) inside the reservoir holder.

The manual drive member is directly or indirectly coupled to the plunger rod of the second reservoir unit. That means an advancing movement of the manual drive member is converted into an advancing movement of the plunger rod.

The manual drive unit of the second injection device is manually driven. That means a user has to push, shift, rotate or screw an element or the manual drive member itself to dispense the medication. Alternatively, the manual drive member is driven by an external device (add-on) releasably attachable to the injection device. In both cases the manual drive unit may be devoid of any automatic drive means such as a spring, a biased elastic element or any kind of motor. In this case the manual drive unit is exclusively hand-driven and manually operated drive mechanism (or driven by the external add-on device), and can be manufactured on low cost. The manual drive unit may be intended for single use and fully disposable. That means the entire second injection device is fully discarded once the reservoir unit has been emptied or after an injection. In contrast to the automatic drive unit and as mentioned above the manual drive unit may be non-releasably connected to the reservoir unit.

In the following description the term “user device” is used and is to be understood to include all electronic devices that are adapted to display information to the user and/or interact with the user (HMI). The term “user device” may include, for example, a mobile device in form of a smart phone, a tablet computer, a pocket computer or a smart watch or it may include augmented reality (AR) devices such as AR goggles or glasses, AR headsets or smart glasses. Furthermore, a user desktop computer or a stationary computing device may be understood as a user device.

In the present context, the terms “substance”, “drug”, “medicament” and “medication” are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances The term “distal” is meant to refer to the direction or the end of the drug delivery device carrying an injection needle or an injection cannula, whereas the term “proximal” is meant to refer to the opposite direction or end pointing away from the needle or cannula.

In a preferred embodiment the reservoir unit further comprises a mechanics holder guiding the plunger rod by splined or threaded engagement with the plunger rod. The mechanics holder is advantageously sleeve-shaped and encloses the plunger rod.

Additionally, the mechanics holder may comprise a resilient member adapted to abut the reservoir and exerting a biasing force to a proximal end of the reservoir. Therefore, the reservoir is biased distally inside the reservoir holder. The reservoir thus is reliably and non-movable hold inside the reservoir unit.

If the injection device comprises an interface member connected to the reservoir unit the mechanics holder may guide the plunger rod inside the interface member and positions the plunger rod relative to the interface member.

Additionally, the first injection device may include a signaling unit connected to the first automatic drive unit and including a visual or optical signaling means for signaling an injection status or injection information.

The injection status may include any of a device status of the injection device, a delivery status of a medication dispensing process, alerts, warnings or messages for the user.

In a preferred embodiment the light signaling means may be simple and limited to a few Light Emitting Diodes LEDs in traffic-light colors. The light signaling means may explicitly exclude any advanced human-machine interfacing (HMI) capability. In particular, the signaling unit may not be wired to, and may be devoid of, a display, screen, or projector for visually transmitting readable or alphanumerical instructions, and likewise exclude an artificial speech assistant for reading out loud the instructions. Therefore, signaling unit is simple and can be produced on low cost.

In a further aspect the injection system includes a third injection device including a third reservoir unit, a second automatic drive unit releasably attachable to the third reservoir unit and including an automatic drive member driven by a power source and adapted to be operatively coupled to the plunger rod of the third reservoir unit. The third injection device further includes a display unit connected to the second automatic drive unit and including a display for displaying an alphanumeric injection status. The first and the third reservoir unit are identical and the first and second automatic drive unit are identical. The display unit replaces the signaling unit of claim 2 and has the same interface (mechanical and electrical) to the automatic drive unit as the latter.

That means the first and third injection device differ only in the signaling or display means but comprise both the same (identical) type of reservoir unit and automatic drive unit. As mentioned above, the first and second injection device differ in the drive unit but comprise both the same type of reservoir unit.

That further allows to reduce production, handling and (final) assembly costs because three different types of injection device use identical sub-assemblies such as the reservoir unit (first, second and third device) and the automatic drive unit (first and third device). There are less different members and components necessary compared to conventional different types of devices having different parts, components or sub-assemblies. Furthermore, the modular system allows to adapt the injection device at manufacturer’s site for a specific purpose or for a specific user group. Namely, different user interfaces (signaling unit, display unit) can be mounted on the same drive unit.

The display unit includes a display, screen or visual projector, for example a liquid-crystal display (LCD) an E-ink display, a LED display or organic light-emitting diode (OLED) display, adapted to display the status information in form of alphanumeric letters, numbers, words or whole sentences. The display may display in black and white or in colors. The display may be partly or fully integrated in a housing of the display unit (e. g. in a sleeve-shaped housing) or it may be attached on an outside of the housing.

In a further aspect, the signaling unit and the display unit have identical interfaces or basis to attach it to the reservoir unit and to the drive unit, respectively. That means the connecting mechanical part (for example a housing) of the signaling unit and the display unit are identical. That again reduces production, handling and assembly costs as there are less distinguishing parts.

The first or third injection device may include a dose setting member for manually setting or correcting a dose. In a further aspect, both the first and third device may include the dose setting member. The dose setting member is connected to the first or second automatic drive unit, respectively. The dose setting member is used by user to set or correct the dose by hand. This is advantageous if the injection device has no access to injection information or is not connected to an external therapy plan that automatically sets the dose. Furthermore, the manual dose setting allows the user to adapted or adjust a predefined dose based on a current situation or circumstances such as eating behavior, sports activities, or personal condition.

The dose setting member may be a dose knob that can be rotated, shifted or screwed relative to a housing of the signaling unit or the display unit to set or correct a dose.

In case the injection device comprises a display unit the dose setting member may be a touch display or touch screen allowing the user to set the dose via display or screen (e.g. LCD).

Alternatively, the injection devices do not comprise any manual dose setting member. In this case the injection device may include a controller that sets the dose based on a therapy plan, on injection information stored in the injection device or received by a data communication from an external device or from a data interface, for example, from information stored in the reservoir unit.

In a preferred embodiment at least the first injection device includes an interface member comprising a connection element for fixing the interface member to the housing of the reservoir unit such that the interface member and the housing form a cavity adapted to hold the reservoir non-movable in place. A reliable fixation of the reservoir relative to the reservoir housing is crucial for a precise dose setting and dose dispensing.

Additionally, the interface member provides for releasable coupling between the automatic drive unit and the reservoir unit. In a coupled state the interface member is at least operatively located between the automatic drive unit and the reservoir unit.

The interface member may include a plunger rod driver adapted to be releasably or non-releasably coupled to the plunger rod and additionally the plunger rod driver includes a coupling element for releasably coupling the plunger rod driver to the automatic drive member if the automatic drive unit is attached to the reservoir unit via interface member. The plunger rod driver may be in threaded or alternatively in splined engagement with the plunger rod. The coupling element may rotationally couple the plunger rod driver to the automatic drive member. The coupling element may be realized as a one or more spline, nut, wedge or groove releasably engageable in a corresponding counter coupling element.

If the modular injection system comprises a third injection device as descripted above the first and third injection device each may include an identical interface member.

The reservoir unit and the interface member may form a sub-assembly. In this case the plunger rod driver is non-releasably connected to the plunger rod of the reservoir unit. In contrast, the coupling between the plunger rod driver and the automatic drive member is releasable as the automatic drive unit is usually used for a plurality of injections (reusable unit) and is used together with different reservoir units (disposable unit). Such a sub-assembly facilitates the production and the handling of the components of the injection device.

The interface member may connect the cartridge holder and a possibly additional components of the reservoir unit to a pre-assembled dispensing unit. The dispensing unit including the reservoir unit and the interface member is easy to handle. If the cartridge is empty after one or more injections the user can replace the dispensing unit (reservoir unit and interface member) as a whole assembly. Besides that, the manufacturer can assembly the cartridge inside the cartridge holder and pre-assemble to a dispensing unit. The latter is easier to store and handle (prevention of breakage of glass) as the cartridge is non-removably fixed and locked inside the pre-assembly.

Alternatively, the first reservoir unit is adapted to be releasably coupled directly to the automatic drive unit without any intermediate member. In this case the automatic drive member is directly coupled to the plunger rod.

If the modular injection system comprises a third injection device the first and third injection device each may include a dispensing unit as descripted above.

Bayonet Connection (No Claim):

In a further embodiment the signaling unit may be additionally connectable to the interface member (and thus to the reservoir unit) by a releasable bayonet connection. For this purpose, the interface member may include a nut or a protrusion adapted to be inserted into the other of the nut or protrusion in the signaling unit.

If the modular injection system includes further a third injection device with a display unit as descripted above also the display unit comprises an identical nut or protrusion as the signaling unit. As mentioned above the signaling unit and the display unit may include each the identical mechanical structure, e. g. a sleeve-shaped housing. Therefore, the bayonet connection elements can be identical for the signaling unit and for the display unit.

The bayonet connection allows an easy and releasable attaching of the automatic drive unit to the interface member and thus to the reservoir unit.

The manual drive unit may include a dose setting member for manually setting or correcting a dose and the manual drive unit may further include a housing at least partially enclosing the dose setting member and the manual drive member. In this embodiment the manual drive unit is devoid of any automatic drive such as drive spring or motors. To dispense a dose the user has to exert directly or indirectly a force to the manual drive member. The manual drive unit can be produced and pre-assembled as a separate unit or sub-assembly and subsequently in a further assembly step can be non-releasably connected to the reservoir unit, preferably without any additional intermediate member.

In a preferred embodiment the manual drive unit may include further a retaining member with an engaging element. The dose setting member, the retaining member and the manual drive member are accommodated in the housing.

In order to set and correct the dose, the dose setting member and the manual drive member can be moved in the longitudinal direction relative to the housing and the manual drive member can be held by the engaging element of the retaining member in a rotationally fixed manner relative to the housing. To dispensing the dose, the manual drive member is released from the engaging element such that the manual drive member can rotate relative to the housing.

The housing further comprises a guide in which guide the holding member can be displaced in the longitudinal direction relative to the housing and is guided in a rotationally fixed manner relative to the housing during dose setting and dose correction.

The releasable engagement between the manual drive member and the housing may be realized by a tooth engagement.

The retaining member enables an easy, reliable and releasable coupling between the housing and the manual drive member. That is, the manual drive member is reliably non-rotatable held during dose setting and dose correction and with a simple axial movement the manual drive member can be released from the housing to be able to rotate and thus to drive the plunger rod to dispense the dose.

In a preferred embodiment the axial movement first rotationally couples the manual drive member and the dose setting member and then uncouples the manual drive member from the housing.

In a preferred embodiment the automatic drive unit comprises an electric circuit with a controller adapted to process data and to control signaling and/or display means.

The automatic drive unit may be an electric motor with a motor shaft and the automatic drive unit comprises further a communication module, where the controller is adapted to control the electric motor based on information or parameters received via communication module from an external sender. The electric motor may be, for example, a stepper motor or a brushless motor (BLDC motor). The controller may be part of an electric circuit, for example, on a printed circuit board (PCB) in the automatic drive unit.

The communication module is adapted to transmit data between the automatic drive unit and an external sender or receiver such as a user device, a server, a cloud server, a computer of a health facility, of a health care practitioner, of an insurance or a computer of an injection device manufacturer or medication manufacturer. For this purpose, the communication module may be wirelessly connected to a data network such as, for example, a local area network (LAN), a wide area network (WAN) or the internet. Alternatively, the communication module can be connected to a router or hub by local WLAN or any another short or near range wireless communication technology such as Bluetooth, ZigBee, WiMAX or NFC and the router or hub is further connected, for example, to the internet, to a cloud server or any other data network.

The information or parameters received for an external sender may include, for example, information about a dose and instructions for the controller to drive the motor for dispensing a predefined dose according to a therapy plan or according to instruction of a HCP.

Additionally or instead the external sender may be a user device such as a smart phone, tablet computer, smart watch or a desktop computer. For example, the user may manually set a dose with an application running on the user device and subsequently transmit the set dose to the drive unit. Consequently, the controller drives to drive unit to dispense the dose based on the injection information received from the user device.

Further examples of the information may be a request for the user to confirm an a injection step via signaling or display unit before the injection can start or the information may include instructions from a HCP, a health insurance or an injection device manufacturer or medication manufacturer.

The information received may additionally be signaled or displayed on a signaling unit or display unit of the injection device respectively or/and displayed on a user device.

In a further embodiment the controller may be additionally adapted to receive injection information or instructions via communication module from an external device and the controller is adapted to process the data and signal the information or control the electric motor accordingly.

The external device may be a cloud server, a computing device of the user or of a healthcare facility or of a HCP, or a computer of an injection device manufacturer or medication manufacturer.

By example, a therapy plan or instructions from a HCP may be stored on the external device. The controller may receive instructions, warnings (e.g. double injection) or reminders for upcoming, planed or pre-defined injections from the external device. Alternatively, the controller may periodically check or query on its own motion the external device regarding upcoming, planned or pre-defined injections.

Additionally, the automatic drive unit may include injection status sensing means for monitoring an injection status and storage means for storing the acquired injection status information. The injection status sensing means can be realized, for example, in form of linear or rotary encoder for a motor in the drive unit, an acceleration sensor, an inductive or capacitive sensor adapted for sensing a motion of an element inside the injection device such as, for example, the plunger rod, the plunger rod driver, the drive member, a dose sleeve, a member driven by the motor or an element of a motor.

The signal of the sensing means is processed by a controller and the acquired sensor information or injection status information can be stored by the storage means. The sensor signal is representative of a current position of the plunger rod, the automatic drive member, an element of the dispensing mechanism, the piston inside the cartridge or is representative of a distance or movement of these elements. Therefore, the acquired information may be used to control a dispensing movement or to verify a current position of the mentioned elements. The sensing means allow to verify, for example, whether a predefined dose has been fully dispensed.

In case the reservoir unit includes a unique identifier (as described below) which is read by the drive unit the sensor signals can be assigned to the specific reservoir unit by the controller. This means the controller has sensed information relating to a specific reservoir unit and can control the drive unit accordingly. Even if the reservoir unit was detached from drive unit and reattached at a later time the controller is able to display for example the remaining medication or to carry out a specific priming operation.

The sensed injection status may be signaled or display to the user by a signaling or display unit, respectively. Furthermore, the injection status may be transmitted to a user device (for example, smart phone, tablet computer, smart watch, and desktop computer).

The acquired injection status information may be logged and stored in the storage means to document a treatment or procedure. These logging data may additionally transmitted from the drive unit (by the communication module inside the drive unit) to a cloud server and provided to HCP, healthcare facilities or device or medication manufacturer.

In a preferred embodiment the reservoir unit comprises a machine-readable tag, it may be a passive tag, with information on the liquid medication inside the reservoir or with identification information uniquely identifying a specific reservoir unit and the drive unit comprises a tag reader for reading the information of the tag of the reservoir unit.

The machine-readable tag may include an optical code or a non-optical tag, for example, readable by radio frequency systems. An optical code includes an optical bar code or a data-matrix, a QR code label, a color code or tags with object identifier information (for example OID). A non-optical tag may be a Radio Frequency Identification (RFID) tag or transponder, specifically a NFC tag operating according to one of the Near-Field Communication (NFC) standards.

The readable tag contains data including unique tag identifiers such as serial numbers, a production lot number or a name encoded in the tag at the time of tag manufacture in read-only format such that this information cannot be altered once set. The tag may further include a user memory programmable, or writable, at delivery device assembly and providing for at least 300 Bytes of memory space, which is sufficient to store drug information in addition to an exemplary encryption key of 256 Bytes such as according to the RSA2048 encryption scheme.

Accordingly, the tag reader of the drive unit may be equipped with a camera or optical sensor or with an RFID/NFC reading or readout capabilities. The tag reader may be part of an electronic circuit present in the automatic drive unit and arranged to read the tag of the reservoir unit once the automatic drive unit is completely attached to the reservoir unit. The tag may be arranged directly on an outer surface of the reservoir (e.g. on a cartridge) at the time of filling the reservoir with medication by the manufacturer of the medication or the tag may be positioned on an element of the reservoir holder, the mechanics holder or any other member of the reservoir unit and attached at the time of pre-assembly of the reservoir unit.

The information about a specific medication or reservoir unit containing the medication may be stored in a database which the controller of the drive unit can request, for example, by an internet connection or via user device. This allows the controller to unambiguously identify a specific reservoir unit and/or medication in the reservoir unit. If a user attaches a new reservoir unit to the automatic drive unit the controller is thus able to verify whether or not the attached reservoir unit and/or the medication inside the reservoir unit correspond to a predefined criteria based on the read tag. For example, the controller may verify based on the read tag if the medication inside the attached reservoir unit corresponds to the predefined medication in a therapy plan or of the HCP. The mentioned therapy plan or instructions may be previously stored in a storage module in the automatic drive unit or may be stored on a cloud server accessible by the controller of the drive unit.

In case the identified medication of the reservoir unit does not match or correspond to a predefined medication or the use-by date has expired or a user-set dose or the current time does not correspond to a predefined value or therapy plan the controller may inform the user accordingly either via signaling or display unit on the injection device or via a user device which is in data communication with the drive unit. Additionally or instead the controller may block or disable the automatic drive member to avoid any dispensing of the medication.

That provides enhanced safety for the user and ensures that the user only injects the correct medication and/or that the user injects the medication in the correct dose and/or at the correct time.

Instead or additional to the above the controller of the drive unit may receive commands from the tag of the reservoir unit. That is, based on identification information of the read tag the drive unit (the controller) may be adapted to control the electric motor or to signal a notification to the user.

Injection reminders or injection instructions may be depending on, or triggered by the specific identification information in the tag that was read by the tag reader of the drive unit. That means, after reading the tag and sending the identification information of a specific medication (specific reservoir unit) to the external device the controller may receive reminders or instruction specific to this medication, e. g. the therapy plan envisages injections of a first medication only once a week and injections of a second medication once a day. Accordingly, the controller may receive the injection reminders or instructions for the first medication daily and the reminders for the second medication weekly. After receiving the reminders the controller signals the injection reminder or instruction to the user, for example, via signaling unit or display unit on the injection device or/and via user device.

The controller of the drive unit may remind the user of an upcoming injection well before the planed injection time to allow the user to prepare the injection device (manually set or adjust a dose) or to get the injection device ready, for example, to take the injection device out of the fridge in order to meet the required warm up time of the medication.

In a preferred embodiment the reminder has a plurality of escalation levels. A first level may include a notification on the user device reminding the user of an upcoming injection. The notification has to be confirmed by the user on the user device.

A second escalation level may include a notification on the user device which can only be confirmed and/or deleted if the administers the pre-defined dose with the injection device. That is, the notification is only confirmed by a logging entry of the controller of the drive unit after the injection. The notification can be, for example, a warning concerning the set dose or an indication about the time since the last injection.

A third escalation level may include the notification and require the logging entry as in second level and additionally includes notification automatically send to a HCP indicating that the user needs active support with respect to the adherence. Such a notification can be, for example, that the holding time was not respected or the priming was not carried out.

In a further embodiment the tag of the reservoir unit includes a predefined and non-modifiable value for a dose (a so-called fix dose). If the reservoir unit is attached to the automatic drive unit the tag reader of the drive unit reads the dose information provided by the tag and the controller sets the dose accordingly. Consequently, the drive unit dispenses the pre-defined fixed dose if the user starts the injection. In this case, the controller does not need any data connection to a network (e.g. cloud server) or any user input to set the dose. Instead, the dose may be exclusively defined by the tag of the reservoir unit (autarkic system).

This is user-friendly as the user does not have to set or correct the dose. Instead, the user can just attach the (correct) reservoir unit to the automatic drive unit and start the injection.

Alternatively, the tag may include predefined and non-modifiable values for several different doses (variable dose). The value or the size of the dose may vary and it may depend on the number of the already dispensed doses, of the time (daytime, time of year) of the injection or of environmental parameters such as temperature, humidity or atmospheric pressure.

In this case, the tag may include, for example, for each injection with a specific reservoir unit a specific dose value. For example, for a first to a fourth injection a dose value is 0.2 ml and from a fifth injection a dose value is 0.6 ml As descripted above the tag reader reads the tag and the controller sets the dose value accordingly. The user does not have to set the dose but may in exceptional cases manually correct the dose to take into account specific circumstances (environmental circumstances, health condition, eating behavior and the like).

In a further embodiment the tag may include instructions or information to be displayed to the user. After reading the tag the controller of the drive unit may display the instruction or information on a signaling unit (LEDs) or display unit (LCD) of the injection device. Additionally or instead, the read instructions or information may be transmitted to the user device and displayed thereon. The instruction or information may be displayed by the controller just after reading the tag or they may be displayed before, during or after an injection (for example the intake instruction can be displayed after the priming but before the injection)

An instruction may be for example, a holding time indicating the time the injection device has to be hold onto the injection site just after the injection. The holding time usually is depending on the type and in particular the viscosity of the medication. Other examples for instructions are medication use or intake instructions, priming instructions, instructions for storage conditions (temperature, humidity) for the medication or the warm up time or handling instructions for a specific medication. Examples for information are the type or name of the medication, the expiry date of the medication, ingredients or allergenic substances contained in the medication, the name of the supplier, the device manufacturer or medication manufacturer.

Optionally, the tag may include profiled dose information indicating not a constant dose value but a non-constant dose curve or a plurality of dose values in function of time. In this case, the controller controls the automatic drive member to start the dispensing with a first injection or dispensing rate (ml/min) and to end with a second dispensing rate different than the first. For example, the injection rate may be 0.5 ml/min at the beginning and 0.1 m/min at the end of the injection.

Additionally or instead, the profiled dose information may depend on the environmental parameter such as temperature, humidity or atmospheric pressure. For example, if the environmental temperature is below 10° C. the medication is dispensed only with an dispensing rate of 0.1 ml/min. Additionally, the tag may include the above described holding time instruction which are depending on the environmental temperature and are amended and displayed depending on a current temperature.

Additionally or instead, the profiled dose information may depend on the viscosity of the medication. That allows to dispense each medication with the suitable and specific dispensing rate. The tag may contain the corresponding holding time to be displayed with the identified medication as descripted above.

Furthermore, the profiled dose information may depend on a maximum injection pressure of the medication. That allows to dispense each medication with the suitable and specific dispensing rate relative to its maximum dispense pressure. The tag may contain information about the maximum dispense pressure and the inner diameter of the cartridge. Accordingly, the controller of the drive unit can determine a maximum injection force applied by the drive unit.

In a further embodiment the tag includes commands for the drive unit which are carried out by the controller after reading the tag. Such commands may include a blocking time preventing the dispensing of the medication. The blocking times may relate to a specific daytime or may relate a defined time period after attaching the reservoir unit to the drive unit (settle time). The commands may further relate to instructions for heating the medication by a heating module present in the drive unit. In this case the tag may include, for example, the instruction that the medication has to be warmed up to 20° C. before the dispensing can start.

All the above mentioned information or instruction (dose instruction, notification, commands for drive unit) contained in the tag and read by the drive unit have the advantages that the user does not have to manually carry out the action. It can be started automatically after reading or at a pre-defined time. Furthermore, the drive unit does not need any data connection to an external device but can be controlled solely and exclusively by the tag of the attached reservoir unit (autarkic system).

As mentioned above the drive unit may include an electric circuit with a controller. In a further embodiment the controller is adapted to determine the dispensed amount of medication or the amount of medication remaining in the reservoir based on the acquired injection status information by the status sensing means. Subsequently, the controller is further adapted to assign or allocate the determined amount of medication to the corresponding read identification information read by the tag reader from the tag of the reservoir unit.

The controller determines the dispensed medication based on the acquired sensor signals of the sensing means, e. g. based on an advancing movement of the plunger rod or of the automatic drive member. As the controller has the information about the total volume of the reservoir from the tag the controller is able to calculate the amount or dose medication remaining inside the reservoir before or/and after each injection.

The controller assigns or matches the determined dispensed amount of medication, the remaining medication or an injection status information to the corresponding reservoir unit that being connected to the automatic drive unit at the time of the injection. The reservoir unit is unambiguously identified by the identifier provided in the tag. Therefore, the controller is adapted to provide dispensing information form a specific reservoir unit. That is in particular advantageous if the user changes the reservoir unit before the medication inside the reservoir is depleted and the user wants to reattach the reservoir unit at a later time. The controller subsequently stores the status information, the dispensed amount of medication and/or the remaining amount of medication together with the identification information from the read tag in the storage module.

These stored dispensing information or status information may be displayed to the user by a signaling or display unit of the injection device or via user device that is in data communication with the drive unit. Additionally or instead the stored dispensing information or status information may be transmitted from the drive unit to a cloud server as described above.

Furthermore, in that embodiment the controller may be adapted to output an indication if the determined dispensed amount of medication or the determined amount of medication remaining in the reservoir exceeds a predefined threshold. The indication, for example, in form of a light or alphanumeric alert, warning or message or an acoustic signal is signaled if a dose is below or above a predetermined dose threshold. The output may be via signaling unit, display unit connected to the drive unit or via external device after the indication was transmitted from the drive unit to the external device. The latter may be, for example, a user device, a server, a cloud server or a computer of HCP as descripted previously.

The threshold may be defined by the user or it may be set by the external device. The signaled indication and a possible replacement of the reservoir unit is logged by the controller and a corresponding log entry is made in a storage module of the automatic drive unit or instead of or additionally transmitted to the external device.

That helps to organize the injection for the user. The user or/and a HCP may be warned if the reservoir is almost empty or if a specific amount of medication is already administered. The indication send to the HCP or health facility may further help to plan the next steps, to discuss, revise or amend the therapy plan or therapy procedure.

In a further aspect, the threshold may be defined by an injection dose and may be received from an external sender, for example via a communication module of the injection device.

The size of the dose for setting the threshold may be set by the therapy plan defining the doses for the user or it may be set by a HCP or doctor or by the user via external user device which is in data communication with the drive unit. Alternatively, the value of the threshold may be stored in a storage module of the drive unit. In both variants the controller of the drive unit may compare the already dispensed amount of medication or the remaining amount of medication with the threshold before and/or after an injection to be able to signal a notification accordingly.

If, for example, an upcoming predefined dose is larger than the remaining medication inside the reservoir the controller can inform the user proactively and accordingly by signaling a notification or indication. Alternatively, the controller sends the indication if an already dispensed dose with a specific reservoir unit exceeds a threshold.

In any case, the controller of the drive unit may signal the indication some time (hours or even days) before the upcoming planed injection therefore allowing the user to replace the reservoir unit well before the injection or allowing the user to take along an additional reservoir unit for the next injection. The latter means that for the next injection two different reservoirs will be required, which leads to a so-called "split dose".

The indication allows to organize and plan the next injections and to avoid an incomplete or even a loss of an injection caused by an empty reservoir.

In a further embodiment the reservoir unit (and the dispensing unit, if any) and the automatic drive unit each have an unique identifier wherein the controller is adapted to transmit a set of all unique identifiers of the injection device to a database.

The unique identifier is, for example, a serial number, a random number, an alphanumeric name or a code including alphanumeric characters. The identifier of the reservoir unit or of the dispensing unit, if any, is contained in the tag. After reading the tag by the tag reader of the drive unit the controller of the drive unit can transmit all identifier together to the database via communication module.

The controller may transmit all logged events (such as priming, injection, user inputs) together with the set of all unique identifiers in the database. The database may be on a user device, on an external server, a cloud server or a computer of a HCP or healthcare facility or device or medication manufacturer. That allows to record and track at a later time the components or units (reusable and disposable) used for a specific injection.

Additionally or instead the database may be stored in the storage module of the injection device and thus the controller can store all identifiers and logged events directly in the drive unit. In this case a connection to a data network is not required.

The disclosure further relates to a method for preparing an injection device for an injection including the steps of a) Providing a reservoir unit including a reservoir containing medication and providing an automatic drive unit driving a plunger rod for dispensing medication of the reservoir;
b) Reading an identification information from a machine-readable tag of the reservoir unit by a tag-reader of the automatic drive unit;
c) Advancing the plunger rod, by a motor of the automatic drive unit, towards a piston inside until the plunger rod abuts the piston, wherein the drive member is controlled based on the read identification information;
d) Optionally, sensing a motor parameter and stopping the advancing of the plunger rod upon change of the motor parameter;
e) Carry out a priming operation.

The identification information unambiguously identifies the reservoir unit. As descripted above identification information in the tag may be a serial numbers, a production lot number or a name encoded in the tag at the time of tag manufacture. The identification information contains further the volume or size of the reservoir contained inside the reservoir unit.

Based on the information about the volume or size of the reservoir the controller in the drive unit is adapted to drive the plunger rod from an initial or retracted position towards the piston inside the cartridge. The identified volume or size of the reservoir allows the controller to determine the distance the plunger rod has to be moved.

The plunger rod may be moved with a reduced speed if the plunger rod comes to or is close to the piston. That allows a precise positioning of the plunger rod relative to the piston of the reservoir.

The position where the plunger rod abuts the piston is sensed by a motor parameter. As soon as the parameter changes the plunger rod touches or abuts the piston and subsequently the movement of the plunger rod is stopped. At this stage, the plunger rod is positioned relative to the piston and is ready for a subsequent priming operation. The latter is necessary to remove air bubbles from the fluid path. The priming operation includes a small movement of the plunger rod and the plunger to drop out a small amount (some drops) of medication. That allows to release possibly present air out of the reservoir out of the needle attached to the reservoir.

Examples of motor parameter are the motor current, the motor voltage, a detected step loss of a stepper motor or a sudden rise of motor torque or the signal of a force sensor.

The disclosure further relates to a modular semi-disposable injection system including a first injection device including:

a first dispensing unit including a reservoir unit including a reservoir filled with medication, a housing for holding the reservoir and a plunger rod adapted to advance a piston inside the reservoir to dispense the medication, and the dispensing unit further including an interface member connected to the housing and including a plunger rod driver coupled to the plunger rod;

a first automatic drive unit releasably attachable to the dispensing unit and including an automatic drive member driven by a power source and adapted to be releasably coupled to the plunger rod driver;

a display unit non-releasably connected to the first automatic drive unit and including a signaling unit including a light signaling means for signaling an injection status of the first injection device;

a second semi-disposable injection device including a second disposable dispensing unit;

a second reusable automatic drive unit;

a signaling unit non-releasably connected to the second automatic drive unit and including a light signaling means for signaling an injection status of the second injection device, wherein the first and the second dispensing unit are identical and wherein the first and second automatic drive unit are identical.

The first and second injection devices may be semi-disposable injection devices each including the dispensing unit, which is disposable, the automatic drive unit, which is reusable and connected either to the display unit (first injection device) or to the signaling unit (second injection device), respectively.

In that embodiment the dispensing unit includes a reservoir unit. This reservoir unit may be (separately) pre-assembled. This may be advantageous if the reservoir unit is additionally used for other types of injection devices, such as fully disposable injectors. In this case the reservoir unit may be a sub-assembly and stored separately. In a further assembly step the reservoir unit can be connected to the interface member for forming the dispensing unit for the semi-disposable injection device. That means the sub-assembly of the reservoir unit allows an optimization of the assembly and logistic processes.

As described above the signaling unit and the display unit may include each the same mechanical basis to be connected to the drive unit and releasably coupled (e.g. bayonet connection) to the dispensing unit. The modular injection system allows a cost effective production, handling and final assembly as mentioned above.

The modular semi-disposable injection system described in the previous section can include the same embodiments and features as the modular injection system descripted further above.

In certain embodiments, the automatic drive unit includes an electric circuit operating in at least two alternative modes, including a priming mode in which a priming operation can be executed and/or can be confirmed, and a needle mode in which mounting of a needle assembly and/or a needle unit can be executed and/or can be confirmed. The electric circuit is switched to the priming mode when successful mounting of an unused needle assembly and/or needle unit is confirmed by the user and/or detected by suitable detection means of the device.

The needle assembly and/or needle unit can be formed as a safety needle assembly including a cylindrical needle housing with a bottom surface supporting a needle cannula and a shield telescopically movable relative to the needle housing. A spring is located within the needle housing and urges the shield in a distal needle covering direction. A locking member is also provided inside the needle housing and automatically and irreversibly locks the shield in a position where the sharp end of the needle cannula is concealed. The needle assembly may be mounted onto a thread at a distal end of the reservoir holder.

In general, to dispense a set dose the user pushes a dispensing button, a dose knob or a dosage knob. The manual or automatic drive unit includes the dispensing button, the dose knob or the dosage knob. However, in the present context, product dispense may alternatively be triggered by displacing the reservoir unit, or at least the reservoir holder, with respect to the drive unit, without any further activity executed by the user, such as depressing a dispensing button. When the needle cannula has fully penetrated the injection site the cannula support of the needle assembly touches the injection site. Continued pressure by the user on the drive unit of the device is then able to shift the cannula support and the reservoir holder onto which the needle assembly is mounted, and optionally the entire reservoir unit, in proximal direction. Even a small amplitude of such a shift of the reservoir holder with respect to the drive unit may be detected by suitable switching means, and exploited to start automatic product dispense. It is worthwhile noting that a concurrent shift of the reservoir and the plunger rod, which is the case with the abovementioned reservoir unit including the latter, does not impact the dose accuracy. This triggering mechanism is particularly useful if the dose to be dispensed is set remotely according to a therapy plan, or has been dialed manually in advance. The only handling steps to be performed for administering the dose then include (a) removal of the needle cover and (b) pressing the device against the injection site, which is strongly reminiscent of the straightforward handling of any two-step auto-injector.

Alternatively, the reservoir and/or disposable unit or the manual or the automatic drive unit include a cover which is telescopic in relation to a housing and movable along a longitudinal axis by a spring force. The cover shields the needle assembly and/or needle unit when the cover is in the distal position. The cover may include a locking member which locks the cover in a position where the sharp end of the needle assembly and/or needle unit is concealed (before and/or after injection). The cover is configured to trigger a power source on the manual or automatic drive unit while moving in the proximal direction e.g. when being pressed against the injection site.

The proximal end of the cover may act as the trigger and switches a switch on the automatic drive unit. The trigger may switch the switch by a flipping movement of the switch, pressing movement of the switch or an electronic alignment connection in between, so that the switch is switched into a first switching position. Once the switch is in the switching position the automatic drive unit starts to administrate a medicament by driving a drive member (for example an electric motor) in the automatic drive unit.

When the medicament has been fully delivered to the user, the power source (e.g. a motor) of the automatic drive unit is going to stop under the control of a processor. The processor produces a signal, so that the user becomes aware that the injection is completed. The user will then remove the injection device from the injection site, so that the cover is moved in the distal direction by the spring force. The switch switches into a second switching position so that the reservoir/disposable unit can removed from the automatic drive unit. Another reservoir/disposable unit can be attached to the automatic drive unit. The reservoir/disposable unit change is executed and/or confirmed by an electric circuit and/or detected by a detection means.

BRIEF DESCRIPTION OF THE DRAWINGS

The subject matter of the disclosure will be explained in more detail in the following text with reference to preferred exemplary embodiments which are illustrated in the attached drawings, in which.

The reference symbols used in the drawings, and their primary meanings, are listed in summary form in the list of designations. In principle, identical parts are provided with the same reference symbols in the figures.

DETAILED DESCRIPTION

FIG. 1 depicts an overview of a modular injection system or an injection device family according to the disclosure. The injection devices of the modular system are realized in form of injection pens. The system includes a semi-disposable injection pen 1 with a LC-display (LCD), a semi-disposable injection pen 2 with LEDs and a fully disposable injection pen 3 intended for single use. The modular system thus includes three different types of injection pens, two different semi-disposable pens 1, 2 and one fully disposable pen 3.

In the present description the term "distal" refers to the side where the needle is attached. This is on the left hand side in the figures. The term "proximal" refers to the opposite side and is on the right hand side in the figures.

Figure 2A:
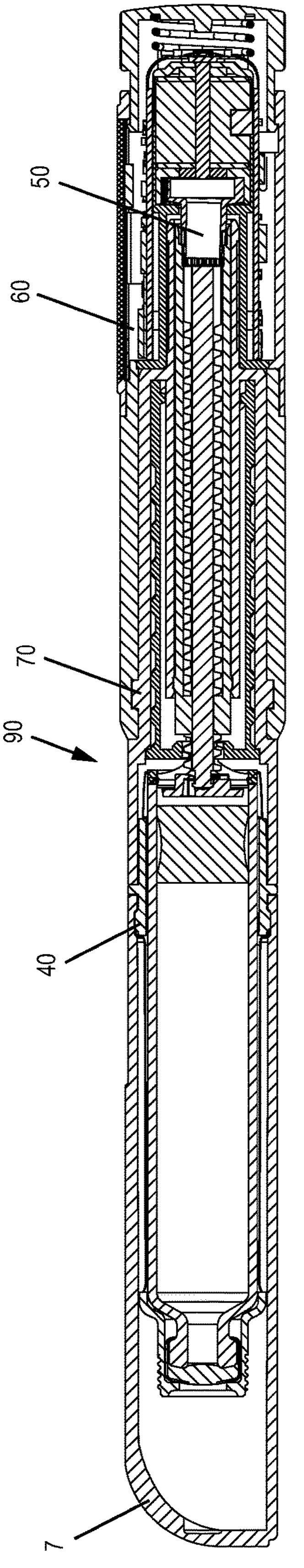
FIG. 2a-c depict the three injection pens of FIG. 1 in a sectional view.
Figure 2B:
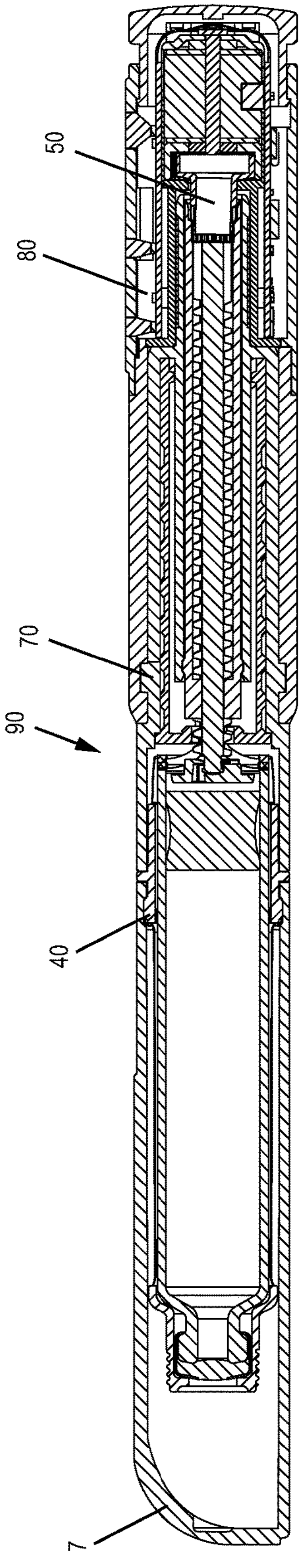
Figure 2C:
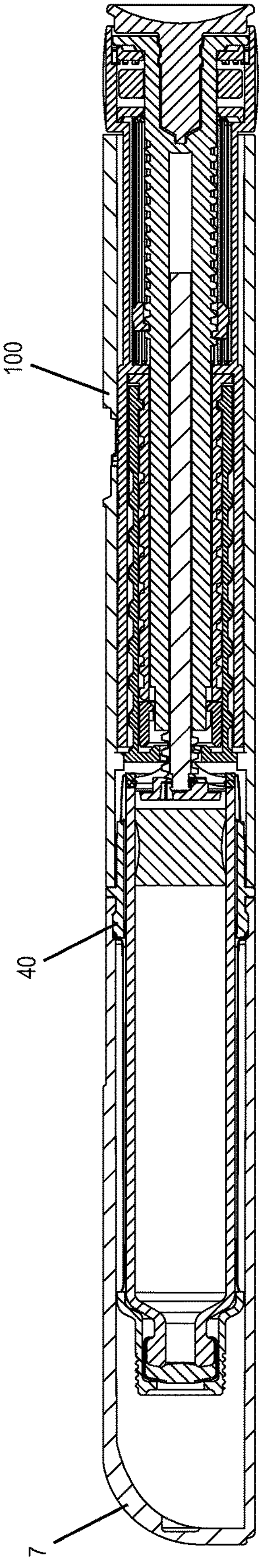

FIGS. 2a to 2c depict each a sectional view of the three types of injection pens 1, 2, 3 wherein the cut runs along a longitudinal axis of the injection pens.

Figure 1A:
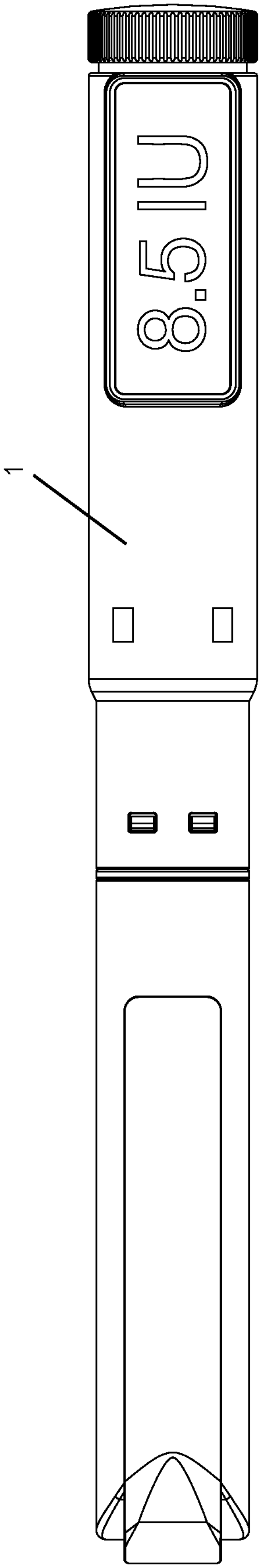
FIG. 1a-c depict an overview of the modular injection system with three different types of injection pen according to the disclosure.

The injection pen 1 with the LCD depicted in FIGS. 1a and 2a includes a disposable assembly and a reusable assembly. The disposable assembly is formed by a dispensing unit 90 including a reservoir unit 40 and an interface member 70. The reusable assembly includes a drive unit 50 and a LCD unit 60. The reusable assembly is releasably attachable to the disposable assembly.

Figure 1B:
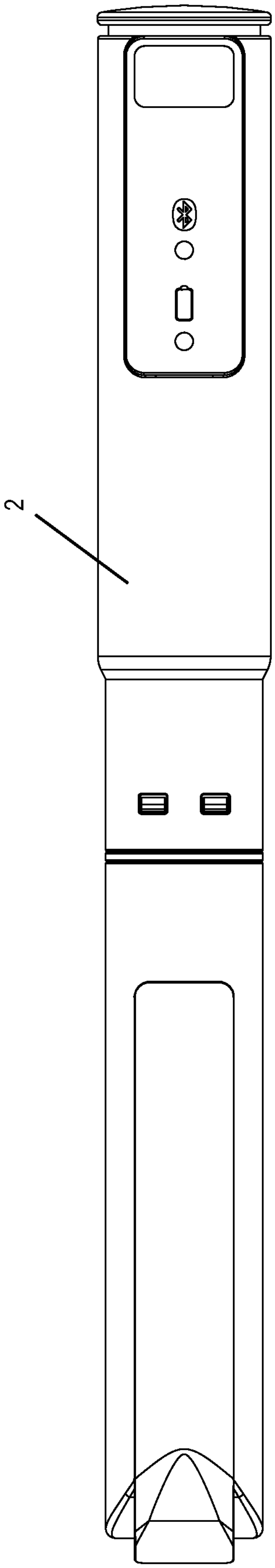

The injection pen 2 with LEDs depicted in FIGS. 1b and 2b includes also a disposable assembly and a reusable assembly. As injection pen 1 the injection pen 2 with LEDs includes a disposable dispensing unit 90 including a reservoir unit 40 and an interface member 70. The reusable assembly includes a drive unit 50 and a signaling unit 80 with LEDs. Similar to injection pen 1 the reusable assembly of the injection pen with the LED is releasably attachable to the disposable assembly.

Figure 1C:
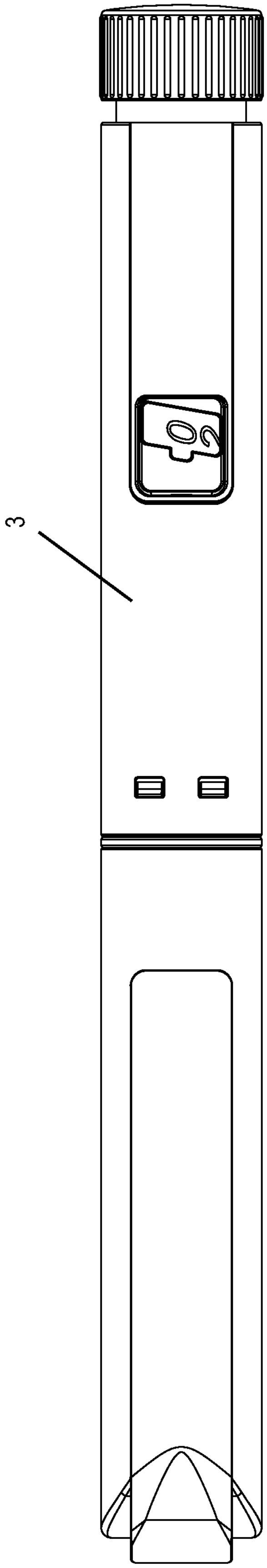

The fully disposable injection pen 3 depicted in FIGS. 1c and 2c includes a reservoir unit 40 and a manual drive unit 100 non-releasably connected to the reservoir unit 40.

The injection pens 1, 2, 3 include sub-assemblies and components that are present in all three or in two pens. That means the pens have some sub-assemblies or components in common. Namely, the three different types of injection pen 1, 2, 3 include each an identical reservoir unit 40. The two semi-disposable pens 1, 2 (pen with LCD and pen with LED) additionally include an identical drive unit 50 but they have different display means mounted onto the drive unit 50. The semi-disposable pen 1 and 2 include an identical pen cap 7.

In the following the three different pens 1, 2, 3 are descripted in detail. Firstly, the structural features of the injection pens are explained. Secondly, the use of the pens, in particular the connectivity with an external cloud server is described.

Figure 3:
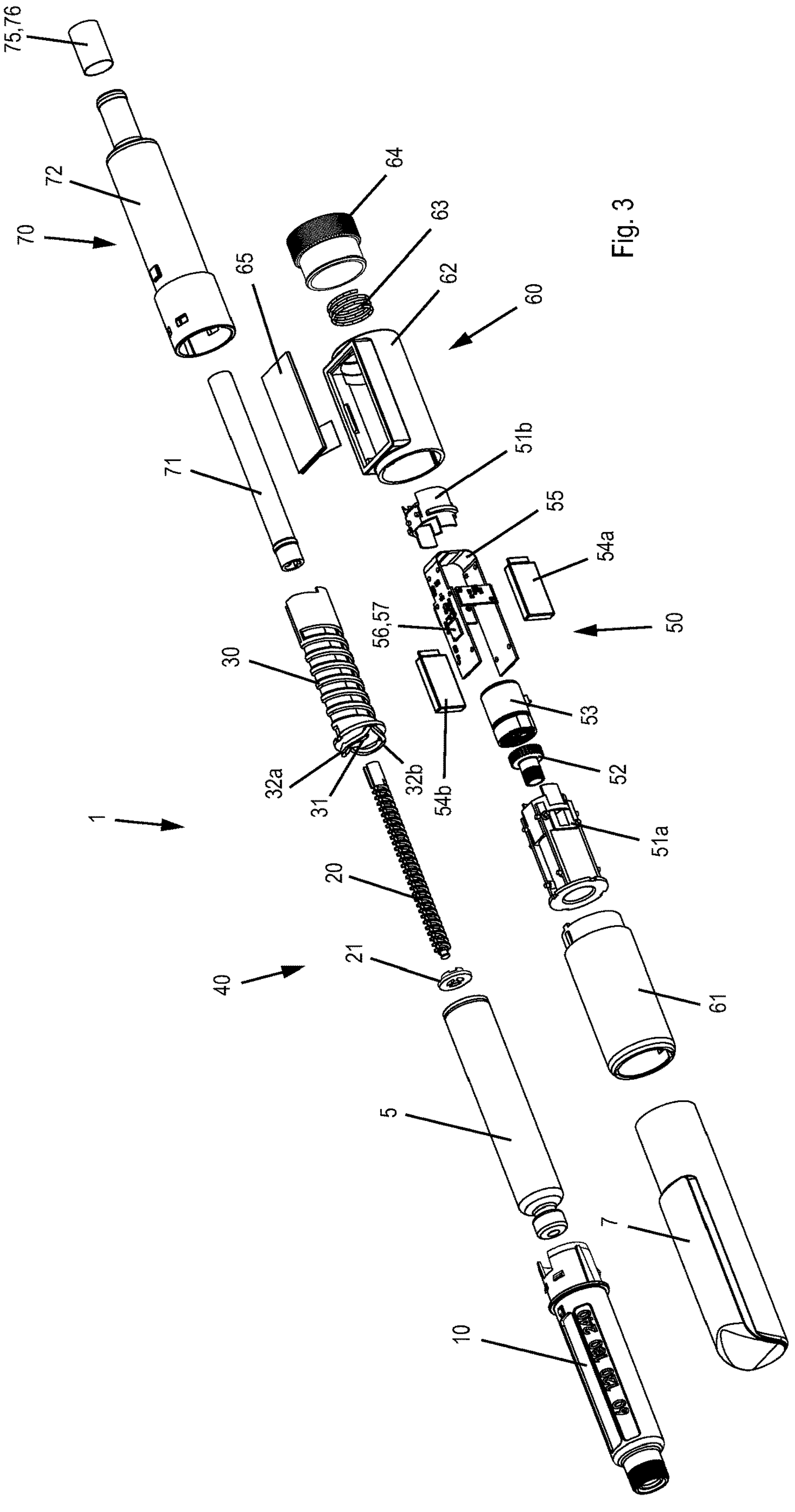
FIG. 3 depicts an exploded view of a semi-disposable injection pen with LCD.
Figure 4:
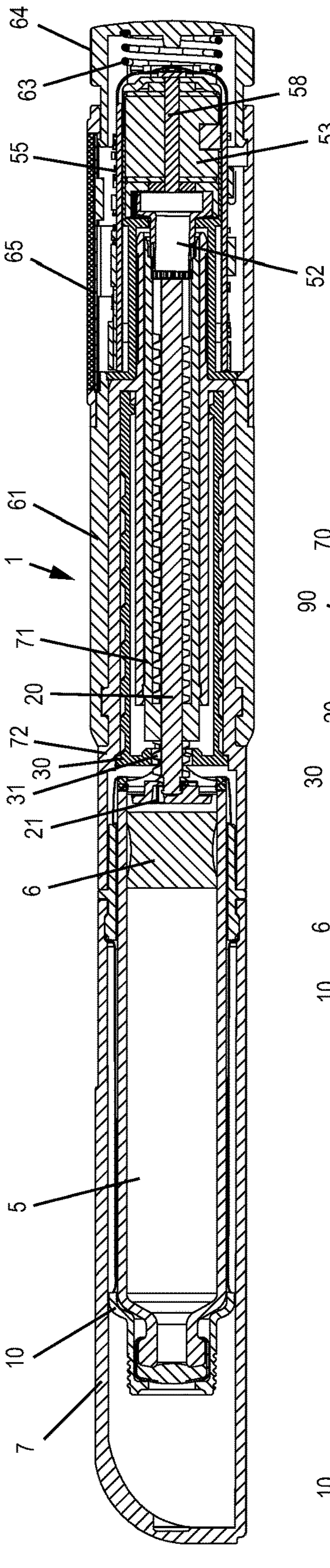
FIG. 4 depicts a sectional view of the semi-disposable injection pen with LCD.

The components of the semi-disposable pen 1 with LCD are descripted with respect to FIG. 3 which depicts an exploded view of the semi-disposable pen 1 also shown in FIGS. 1a and 2a. FIG. 4 depicts a sectional view of the same pen 1.

As mentioned above the disposable dispensing unit 90 includes the reservoir unit 40 and an interface member 70. The dispensing unit 90 is also depicted separately in FIGS. 5a and 5b.

As shown in the exploded view of FIG. 3 the reservoir unit 40 includes a reservoir holder 10 (or cartridge holder), a reservoir in form of a cartridge 5 containing medication, a mechanics holder 30 and a plunger rod 20 with a flange 21 pivotally mounted on a distal end of the plunger rod 20. The plunger rod 20 includes a thread along its longitudinal shaft. A nut extending along the shaft is adapted to be in engagement with a drive member.

A thread 31 integrally formed in the mechanics holder 30 holds the plunger rod 20 in threaded engagement with the mechanics holder 30. In an assembled state the flange 21 of the plunger rod 20 abuts a piston 6 (see FIG. 4) inside the cartridge 5. The mechanics holder 30 is sleeve-shaped and includes an end wall or flange on its distal side. The end wall has a centered opening including the thread 31 is located. On the distal side of the end wall the mechanics holder 30 includes two half ring-shaped elements 32a, 32b that are connected to the end wall. The ring-shaped elements 32a, 32b are elastically deformed if a reservoir 5 is hold in the reservoir holder 10. Therefore, the ring-shaped elements bias the cartridge 5 in a distal direction and hold the cartridge 5 non-movable inside the reservoir holder 10.

The reservoir holder 10 includes at its distal end a thread for mounting a needle assembly (not shown). On its proximal end the holder 10 has snap lock elements for connecting the holder to the interface member 70.

The dispensing unit 90 includes further the sleeve-shaped interface member 70 enclosing the mechanics holder 30 and the plunger rod 20. An interface member housing 72 is non-dissociable or non-releasably connected to the reservoir holder 10 by a snap lock. The reservoir holder 10 is thus fixed relative to the interface member and encloses and holds the cartridge 5 non-movable between an inner distal end of the reservoir holder 10 and the distal end wall of the mechanics holder 30. The interface member 70 includes the housing 72 and a plunger rod driver 71 coaxially arranged and guided inside the housing 72. The plunger rod driver 71 is splined to the plunger rod 20 such that it is rotationally fixed but axially movable relative to the plunger rod 20. At the proximal end the plunger rod driver 71 includes circumferentially arranged teeth 73 adapted to be rotationally coupled to a drive member 52 of the automatic drive unit 50 in the reusable assembly.

The interface member 70 includes on its outer surface or integrally formed a machine-readable tag 76 in form of a NFC tag that is readable by a tag reader of the drive unit 50 if the drive unit 50 is attached to the dispensing unit 90. In the embodiment shown in FIG. 3 the tag 76 is arranged on a label 75. Alternatively, the tag 76 can also be placed onto a surface of the cartridge 5. In an alternative embodiment the tag can be a bar code, a QR code or a color code. The tag includes the following information of UDI code, medication type and name, expiry date and volume of the cartridge 5. Furthermore, a needle unit (not shown) mounted to the reservoir holder 10 includes also a tag with a unique identifier allowing the controller to identify the (mounted) needle unit.

Figure 5A:
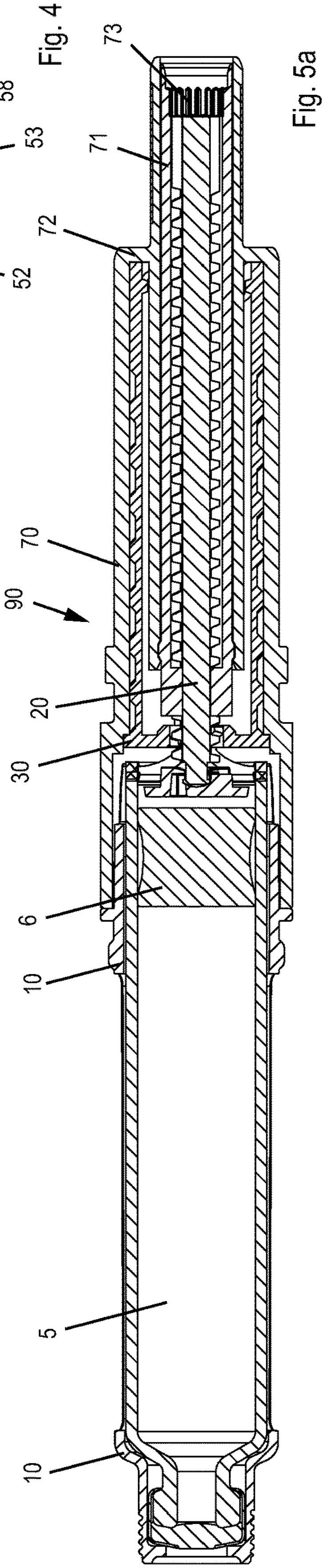
FIG. 5a depicts a sectional view of the dispensing unit.
Figure 5B:
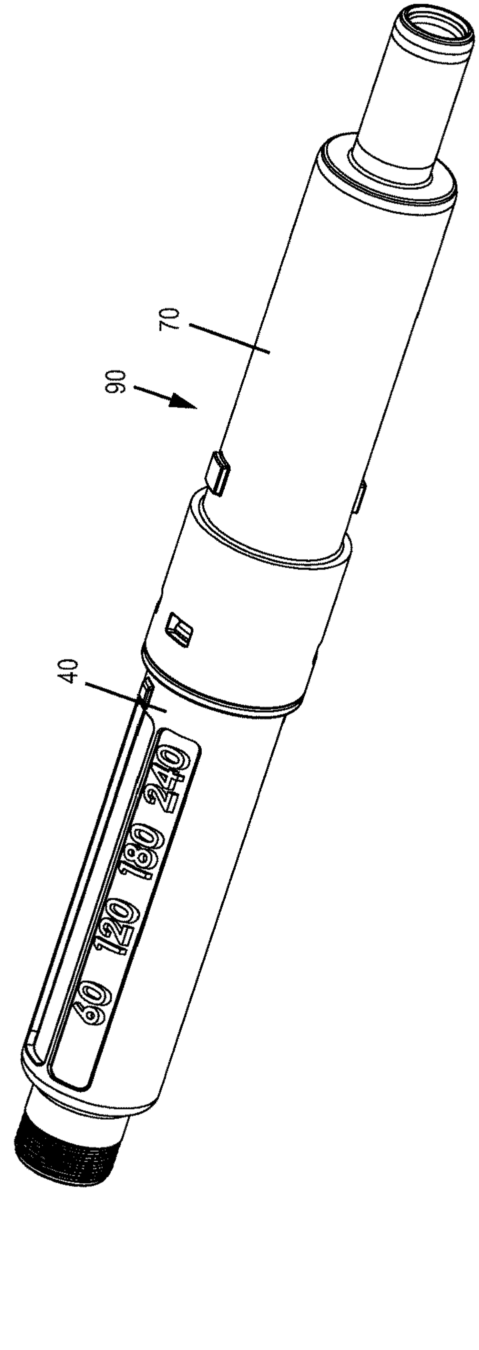
FIG. 5b depicts a perspective view of the dispensing unit.

The disposable dispensing unit 90, as shown in FIGS. 5*a* und 5*b* can be produced, pre-assembled and stored separately from the reusable assembly. That is, the reservoir unit 40 and the interface member 70 may be produced by a device manufacturer and delivered to the medication manufacturer. The latter inserts the filled cartridge 5 in the reservoir holder 10 and pre-assembles the single components to a sub-assembly, namely to the dispensing unit 90. The cartridge 5 is non-movably hold inside the holder. If the dispensing unit 90 attached to the reusable assembly (drive unit 50 and display unit 60) the plunger rod 20 can be moved towards the piston to prepare the dispensing unit 90 for the first injection. Alternatively, the plunger rod 20 positioned next to the piston at the time of assembly and thus a so-called factory priming can be provided.

The reusable assembly of the injection device 1 includes the automatic drive unit 50 and the display unit 60. The automatic drive unit 50 (separately depicted in FIGS. 6*a*, 6*b* and 6*c*) includes a support structure 51*a*, 51*b*, an electric motor 53 with a motor shaft 58 (FIG. 4), in particular a BLDC motor o stepper motor, for moving the plunger rod 20, a sleeve-shaped automatic drive member 52, a gear connecting the motor shaft 58 and the automatic drive member 52, a printed circuit board (PCB) 55 with a controller (not shown) for controlling the electric motor, an energy source in form of a rechargeable battery 54*a*, 54*b*, a tag reader (not shown), a data storage module 57, a communication module 56 and sensing means in form of an encoder (not shown) for sensing the movement of the motor shaft 58 and thus the movement of the plunger rod 20.

Figure 6C:
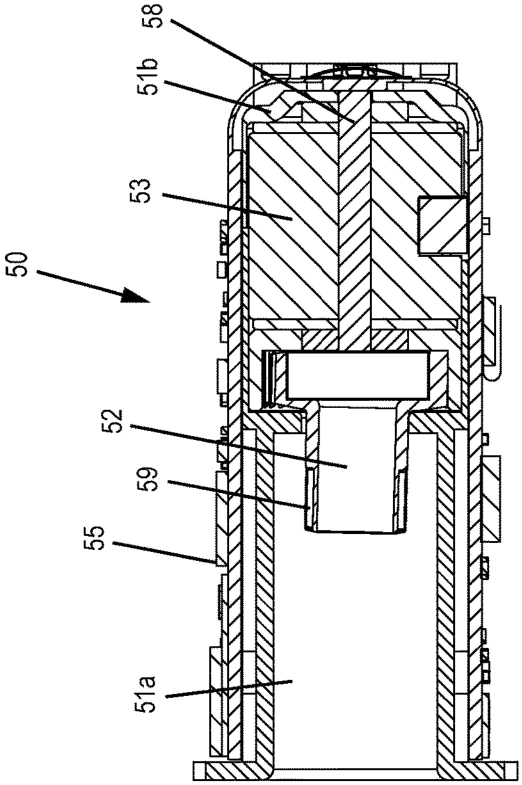
FIG. 6a-c depict the drive unit in a perspective view and in a sectional view.
Figure 6A:
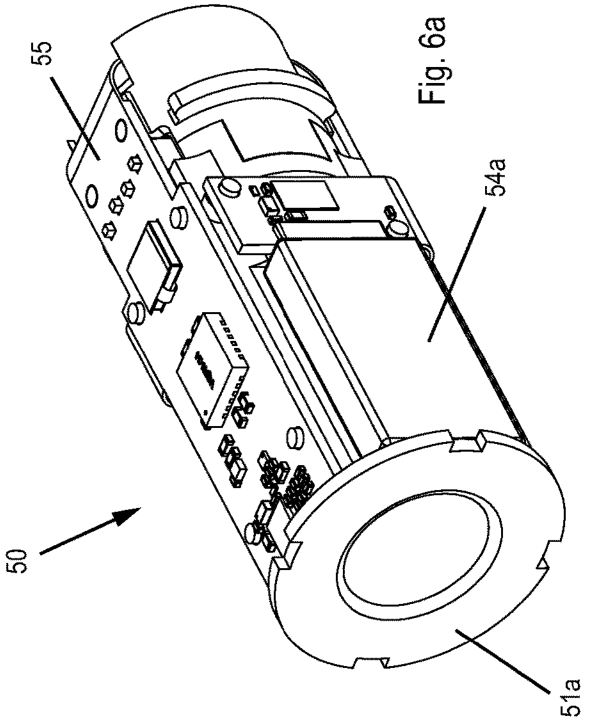
Figure 6B:
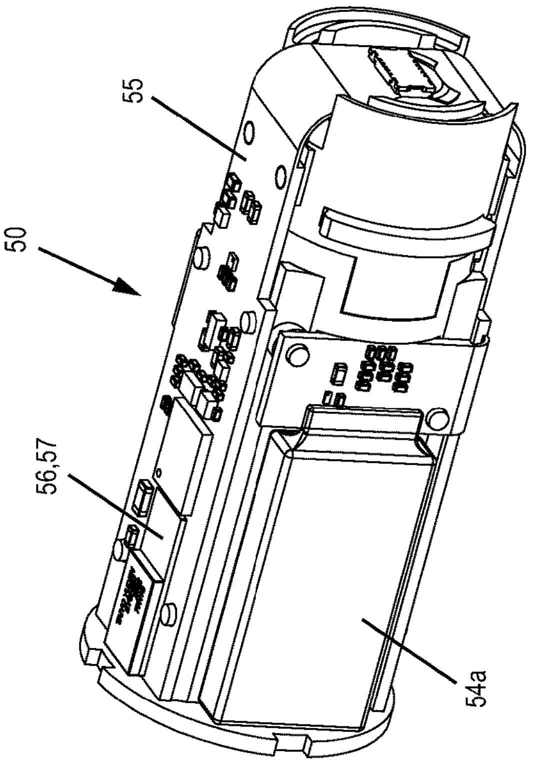

As shown in FIG. 6*c* depicting the automatic drive unit 50 the motor 53 is arranged in a proximal end portion of the automatic drive unit 50. The PCB 55 with the controller is attached to an outside of the support structure 51*a* and the rechargeable battery 54*a,b* of the embodiment shown in FIG. 3 includes two battery packs located on two opposite sides of the support structure 51*a*. The motor shaft 58 is coupled to the automatic drive member 52 by the gear. The sleeve-shaped drive member 52 includes distally and circumferentially arranged teeth 59 (FIG. 6*c*) adapted to be coupled to the proximal teeth 73 of the plunger rod driver 71 if the reusable assembly is attached to the dispensing unit 90.

The communication module 56 is adapted to transmit data between the drive unit 50 and an external device such as a cloud server or a user device in form of a computer, a smart phone, a tablet computer, a smart watch, smart glasses or the like. That means the communication module 56 can receive or send data generated and/or stored in the storage module 57. The communication module 56 is connected to the external device wirelessly, for example, by a wireless local area network (WLAN) or by another short or near range wireless communication technology such as Bluetooth, ZigBee, WiMAX or NFC. In an alternative embodiment the communication module includes a cellular network module such as GSM, LTE or NR for direct and independent internet access.

The tag reader can read the tag of the dispensing unit 90 if the latter is attached to the reusable assembly. Depending on the embodiment the tag reader is adapted to read the NFC tag, the bar code, the QR code, OID or the color code of the dispensing unit. The read tag information (parameter) are subsequently processed by the controller.

Furthermore, the drive unit 50 includes itself a tag (not shown) including a unique identifier that can be read, for example, by an add-on device releasably attachable to the injection pen 1.

The automatic drive unit 50 is coaxially enclosed by the sleeve-shaped display unit 60 and non-dissociable or non-releasably connected thereto. The display unit 60 includes a distal and proximal housing 61, 62, a LCD 65, a spring 63 and a dose knob 64. The latter is arranged on a proximal end of the proximal housing 62 and can be used by a user to manually set a dose by rotating the dose knob 64. The dose knob 64 is further axially moveable to the housing and biased in a proximal direction by the spring 63 arranged inside the dose knob. The LCD 65 can display a set or dispensed dose, an injection status, a battery status, instructions for use (IFU) or information read from the tag of the dispensing unit 90 or information received from an external device via communication unit. The LCD 65 is hence electrically connected to the PCB 55 of the drive unit 50. On an inside and distal end portion of the sleeve-shaped distal housing 61 a L-shaped nut is arranged (not shown) forming part of a bayonet connection between the dispensing unit 90 and the display unit 60.

FIG. 4 depicts a sectional view of the semi-disposable injection pen 1. As shown in FIG. 4 the dispensing unit 90 is attached to the automatic drive unit 50 and the display unit 60. In other words the disposable assembly is attached to the reusable assembly forming the injection pen 1. To mechanically attach the disposable dispensing unit 90 to the reusable assembly (dose unit 50 and display unit 60) the proximal cylindrical portion of the interface member 70 is inserted into the sleeve-shaped distal display unit housing 61. During insertion the proximal teeth 73 of the plunger rod driver 71 get into contact with the distal teeth 59 of the automatic drive member 52 and thereby rotationally coupling the plunger rod driver 71 to the drive member 52. Furthermore, a protrusion 74 (FIG. 5*b*) located on an outside of the interface member housing 72 is inserted in the L-shaped nut of the display unit housing 61. With a rotational movement of the dispensing unit 90 relative to the drive unit 50 and display unit 60 the dispensing unit is mechanically connected to the display unit 60 and the drive unit 50 by the bayonet connection.

A dose is set either manually by the user or automatically by instructions of a therapy plan or based on instruction of the medication manufacturer via cloud server or by information read from the tag of the dispensing unit. To manually set a dose the user rotates the dose knob 64. To correct a dose the dose knob 64 can be rotated in a counter direction. The set dose is displayed on the LCD 64 and additionally on the user device as the controller transmit the data via communication module 56 to the user device. Additionally, the controller logs the set and dispensed doses and transmits a log entry to the cloud server.

In normal operation the dose is set automatically. The controller periodically request injection information form the cloud server via user device. At least if the user replaces the dispensing unit and attaches a new dispensing unit to the reusable assembly the controller request the injection information. These information contain the time and the amount of the dose of the next upcoming injection. After receiving the information via user device the controller sets the dose and displays it on the LCD. The dose is additionally displayed on the user device.

For both cases, for the manual setting and for the automatic setting the user only has to initiate the injection process by pushing the dose knob 64.

An example of a use case is descripted with respect to the FIGS. 11, 12*a* and 12*b* further below.

Figure 7:
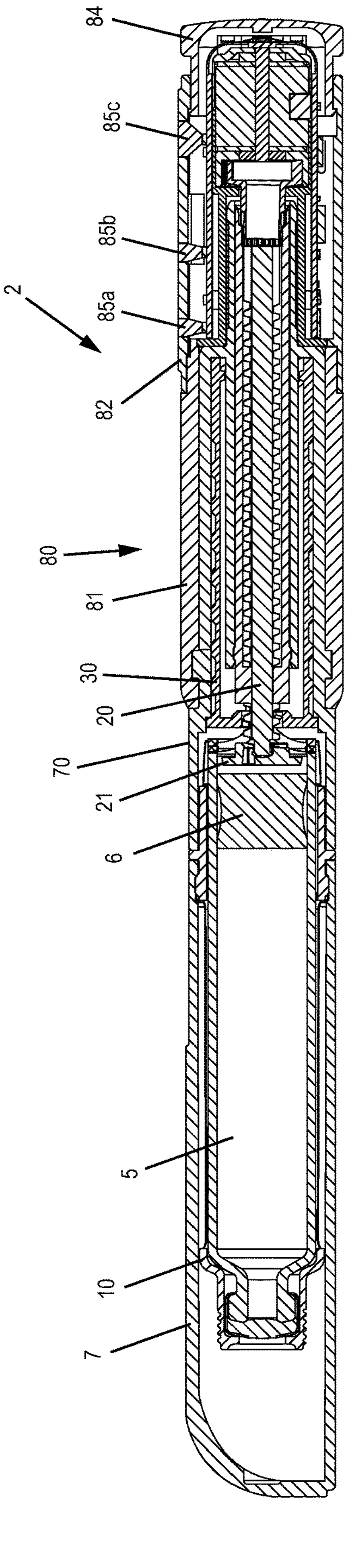
FIG. 7 depicts a sectional view of the semi-disposable pen with LEDs.

FIG. 7 depicts the semi-disposable injection pen 2 with LEDs. As mentioned above the pen 2 has an identical dispensing unit 90 and an identical drive unit 50 as the injection pen 1 with the LCD.

However, the dose unit 50 of the injection pen 2 is connected to a signaling unit 80 instead of a display unit. In contrast to the display unit 60 the signaling unit 80 is devoid of any display or screen and includes only three LEDs 85*a*, 85*b*, 85*c* indicating the injection status, the battery status and the connection (Bluetooth) status. The three LEDs 85*a*, 85*b*, 85*c* are depicted in FIG. 1*b*. There is a light path or a light guide (shown in FIG. 7) for each LED 85*a*, 85*b*, 85*c* to guide the light from the PCB 55 to an outer surface of a proximal housing 82.

A further difference is that the injection pen 2 does not include a rotatable dose knob. As depicted in FIG. 7 the signaling unit 80 has a dispensing button 84 that can be pushed in the longitudinal direction by the user to initiate or start an injection. The signaling unit 80 is hence less complex and can be manufactured on lower cost compared to the display unit 60.

All other features of the injection pen 2, in particular the bayonet connection and the coupling between the automatic drive member 52 and the plunger rod driver 71 are identical to the injection pen 1 with LCD.

The upcoming injection or injection information are signaled to the user by the LEDs. A green LED is activated to signal that the dose is ready for injection. The value of the dose is displayed on the user device. LEDs of other colors (orange, red) signal the user an error condition, an expired used-by date or that a wrong dispensing unit is attached to the reusable assembly. The codes of the colors are displayed on the user device.

Figure 8A:
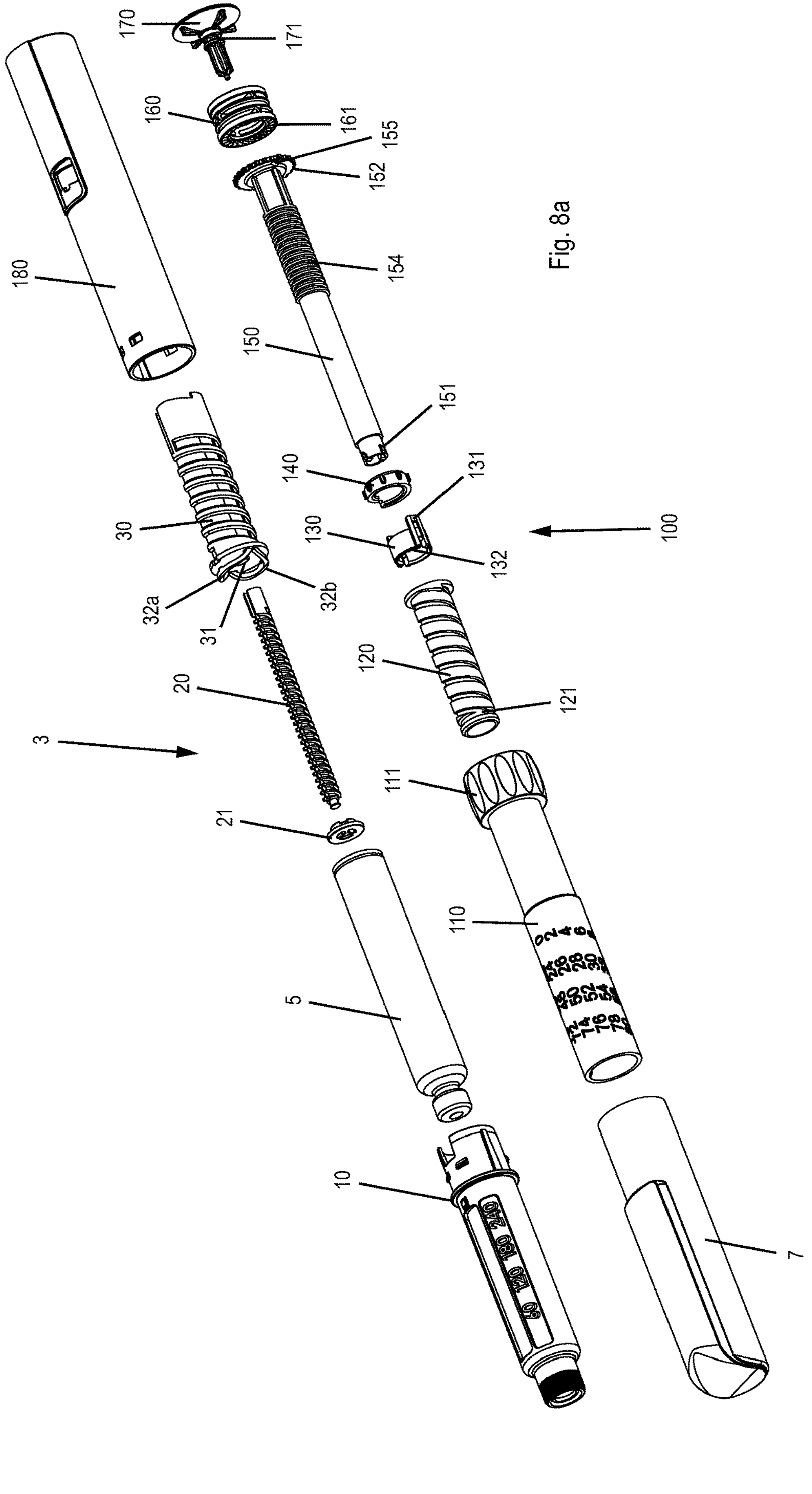
FIG. 8a depicts an exploded view of a fully disposable injection pen.

The fully disposable injection pen 3 according to the disclosure is depicted as an exploded view in FIG. 8*a*. FIGS. 9*a* and 9*b* depicts a sectional view of the disposable pen 3. In the following the structural features are descripted in detail with respect to FIGS. 8 and 9. Subsequently, the function and in particular the setting and correction of a dose are descripted.

The fully disposable injection pen 3 includes the removable cap 7 and the reservoir unit 40 which is identical to the reservoir unit 40 of the semi-disposable injection pens 1, 2. The disposable injection pen 3 further includes a manual drive unit 100.

As mentioned above the reservoir unit 40 includes the reservoir holder 10, the cartridge 5, the plunger rod 20 with flange 21 and the mechanics holder 30. The manual drive unit 100 includes a housing 180, dose sleeve 110 for setting a dose, a dose insert 120, a retaining member 130, a manual drive member or drive sleeve 150, a stop nut 140, a click sleeve 160 and a dispensing button 170.

Figure 8C:
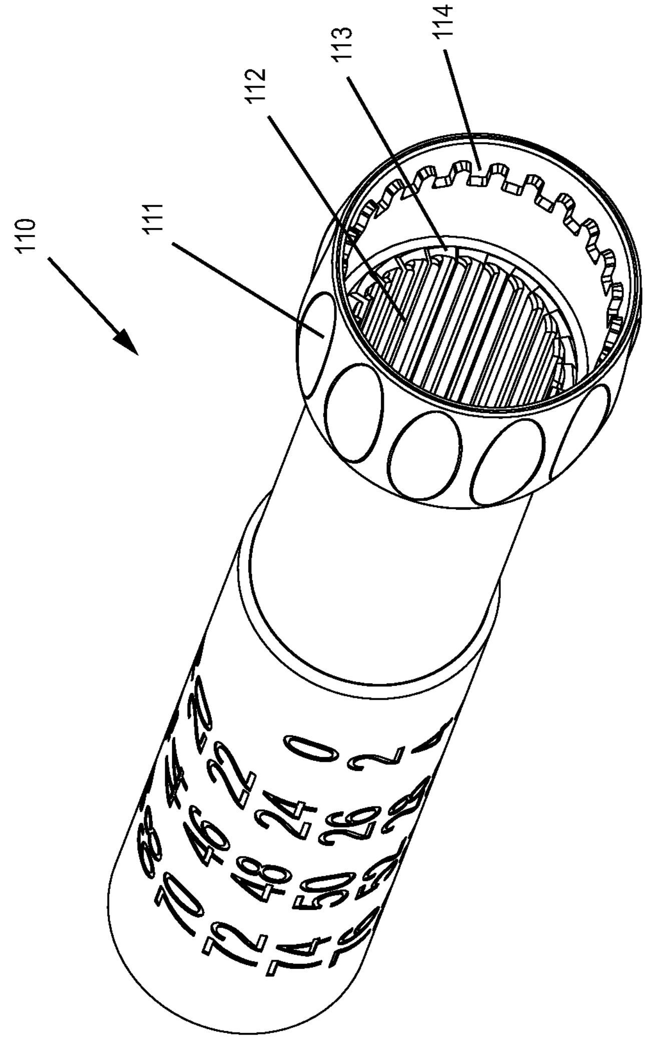
FIGS. 8b and 8c depict a detail view of the retaining member and the dose sleeve.
Figure 9A:
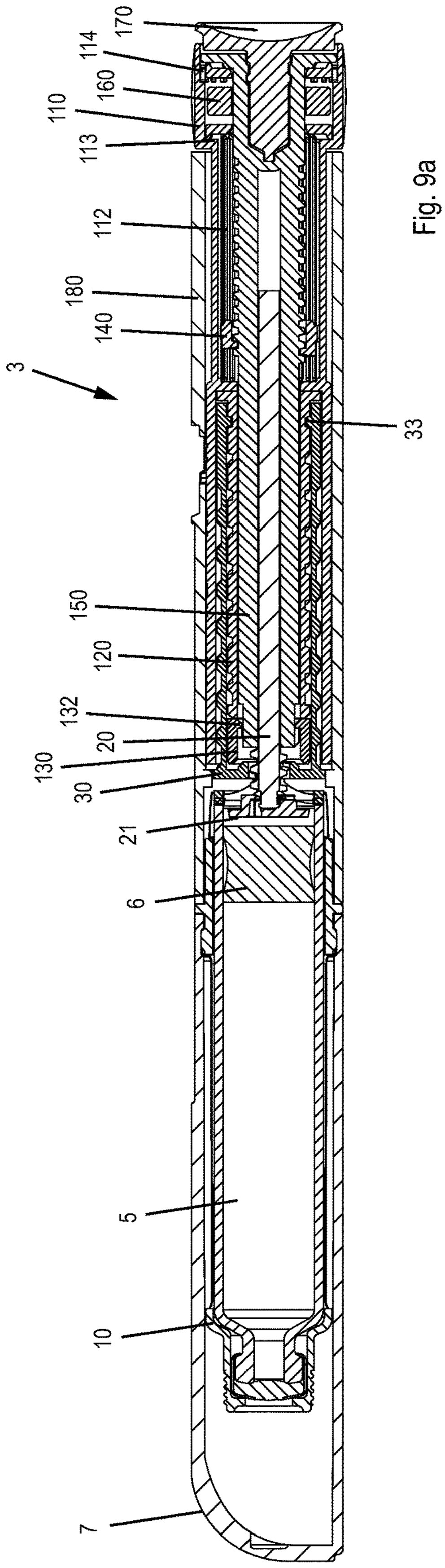
FIG. 9a depicts a sectional view of the fully disposable pen in an initial state.
Figure 9B:
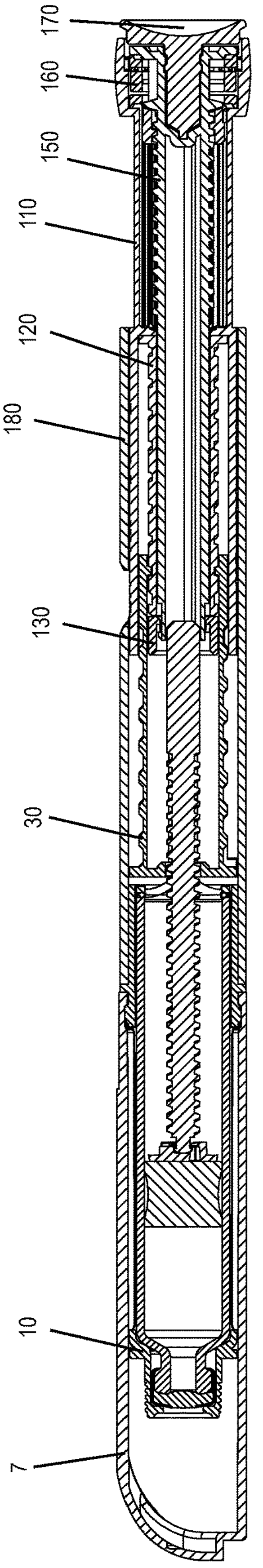
FIG. 9b depicts a sectional view of the pen of FIG. 9a in a state with a set dose.

FIG. 8*c* depicts a detailed view of the dose sleeve 110. The dose sleeve 110 has the form of a hollow cylinder or sleeve and has on its proximal end a larger diameter forming a grip portion 111. On an outer surface of a distal portion are helically arranged numbers that are visible through an opening (dose window) in the housing 180 during dose setting and dispensing. In a distal portion the dose sleeve 110 includes an inner dose insert 120 coaxially arranged inside the dose sleeve 110 and having a smaller diameter than the dose sleeve 110. The dose insert 120 is rotationally and axially fixed to the dose sleeve 110 or in an alternative embodiment integrally formed with the dose sleeve (in one piece as two component part). Between an inner surface of the dose sleeve 110 and an outer surface of the dose insert 120 a cylindrical gap is formed. In this gap the mechanics holder 30 fixed to a housing 180 is accommodated.

On an outer surface the dose insert 120 has a thread adapted to engage a radially inward protruding thread element 33 (see FIG. 9*a*) of the mechanics holder 30. The dose insert 120 and the dose sleeve 110 are therefore in threaded engagement with the mechanics holder 30.

On a distal end the dose insert 120 includes a circumferential nut 121 (FIG. 8*a*). The retaining member 130 includes a corresponding hook element 131 adapted to engage the nut 121. The retaining member 120 is therefore axially coupled but rotationally free relative to the dose insert 120 and the dose sleeve 110. Furthermore, the hook element 131 guides the retaining member in a groove on an inside of the mechanics holder 30 such that the retaining member is rotationally fixed relative to the mechanics holder but axially moveable thereto.

The dose insert 120 has further a stop element in form of a ramp arranged on an outer distal end portion. The stop element abuts a counter ramp element of the mechanics holder 30 in an initial or retracted positon of the dose insert 120. The ramp elements form thus a first or minimal stop for the dose sleeve. The dose sleeve 110 has on its inside a radially protruding stop element (not shown) adapted to engage a counter stop element on an outer surface of the mechanics holder 30 (not shown). The stop element abuts the counter stop element if the dose sleeve 110 is screwed out to an end position.

In a proximal portion the dose sleeve 110 includes on its inside axially extending nuts 112 (FIG. 9*a*) in which the stop nut 140 is in splined engagement and is axially guided. Proximal to the nuts 112 the dose sleeve 110 has a larger inner diameter. Thus an inner radial wall is present between the nuts 112 and the portion with the larger diameter. On this inner wall are saw teeth 113 (FIG. 8*c*) circumferentially arranged and adapted to engage counter saw teeth 161 of the click sleeve 160 as descripted below. At the proximal end the dose sleeve 110 has on its inside circumferentially arranged radial nuts 114 adapted to accommodate radial 155 teeth of the drive member.

Figure 8B:
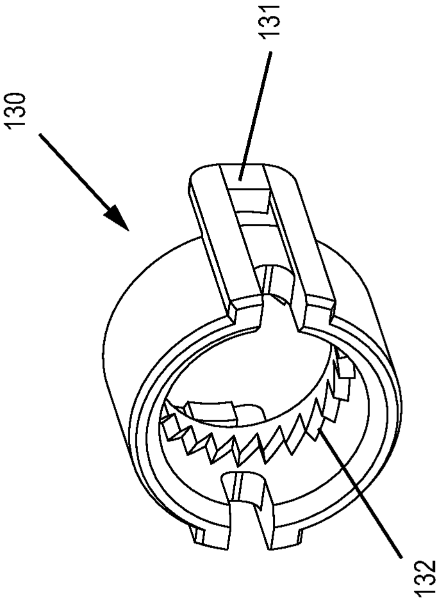

FIG. 8*b* depicts a detailed view of the retaining member 130. It is sleeve-shaped and is axially fixed to the dose sleeve 110 by its hook element 131 as descripted above. The retaining member 130 is splined to the mechanics holder 30 and thus rotationally fixed thereto but axially moveable relative to the mechanics holder 30 (and thus to the housing 180). On an inside the retaining member 130 has nuts 132.

The sleeve-shaped manual drive member 150 includes on its distal end a portion with a smaller outer diameter. In this portion are circumferentially arranged protrusions 151 adapted to be engaged with the corresponding nuts 132 of the retaining member 130. A proximal portion of the end portion (axially in-between teeth and larger diameter of drive member) is smaller than the most inner diameter of the retaining member 130 such that the retaining member 130 is not engaged with the drive member 150 if it is axially positioned at this distal end portion, e. g. if the drive member 150 is in a released position during dose dispensing (explained below).

On a proximal portion the drive member 150 includes an outer thread 154 for the stop nut 140. Proximal the outer thread 154 of the drive member includes a cylindrical portion for guiding the click sleeve 160. The cylindrical portion ends on a proximal end with a flange 152 forming a proximal end of the drive member 150. On a distal directed side of the flange 152 are saw teeth 153 circumferentially arranged and adapted to engage corresponding saw teeth on the clicker sleeve 160. On its outer circumference the flange 152 has radial teeth 155 protruding radially outward and adapted to engage in the radial nuts 114 inside the dose sleeve 110.

The drive member 150 has an opening or blind bore in the longitudinal direction from the proximal end. In this bore the dispensing button 170 is guided.

From a distal end the drive member 150 has also a blind bore in the longitudinal direction with an inner axial spline adapted to rotationally couple the drive member 150 to the plunger rod 20 but allowing the drive member 150 to be axially shifted relative to the plunger rod 20.

The click sleeve 160 is coaxially positioned around the cylindrical portion of the drive member 150. The click sleeve 160 includes slits or recesses in its cylindrical body allowing the click sleeve 160 to be elastically deformed in a longitudinal direction. On the click sleeve distal front and on the proximal front circumferentially arranged saw teeth are present. Distal teeth 161 are adapted to ride over or engage counter saw teeth 113 on the dose sleeve 110 and proximal saw teeth (not shown) are adapted to ride over or engage counter saw teeth 153 of the flange 152 of the drive member 150. The click sleeve 160 is slightly compressed and axially sandwiched between the radial wall of the dose sleeve 110 and the flange 152 of the drive member 150. As the click sleeve 160 is elastically compressed it biases the drive member 150 in a proximal direction. An axial movement of the drive member 150 is limited by the nuts 132 of the retaining member 130.

The dispensing button 170 is t-shaped with a shaft and a flange and is hold and guided by the blind bore of the drive member 150. The shaft has a circumferentially extending rib 171 and the drive member blind hole has a corresponding nut accommodating the rib 171. The dispensing button 170 is thus axially fixed but rotationally free relative to the drive member 150.

The stop nut 140 is ring-shaped and includes on its inner diameter a thread element adapted to engage the outer thread 154 of the drive member 150. On its outer surface the stop nut 140 includes protrusions engaging the longitudinal nuts 112 of the dose sleeve 110 which rotationally couple the stop nut 140 to the dose sleeve 110. On its proximal end the stop nut 140 includes stop elements that abut corresponding stop elements of the drive member 150 if the stop nut is in an end position.

The described parts of the injection pen 1 are made of plastic as known in the art, for example, polypropylene (PP). The click sleeve 160 can be made of metal or made of plastic.

FIG. 9*a* depicts the fully disposable pen 3 in a start or initial position. To set a dose the user grabs the grip portion 111 and rotates the dose sleeve 110. As the dose sleeve 110 is in threaded engagement with the mechanics holder 30 the dose sleeve 110 is screwed out of the housing 180.

The plunger rod 20 and the drive member 150 rotationally coupled to the plunger rod 20 are not rotated due to the rotational coupling to the retaining member 130. The click sleeve 160 does not rotate either as the steep flank of its proximal saw teeth abut the steep flank of the saw teeth 153 of the drive member 150. As the click sleeve 160 abuts the radial wall inside the dose sleeve 110 both, the click sleeve and the drive member are shifted proximally when the dose sleeve 110 is screwed out of the housing 180.

During dose setting the dose sleeve 110 is rotated relative to the click sleeve 160. Due to the axially and elastically deformable click sleeve 160 the saw teeth of the dose sleeve 110 are able to ride over the distal saw teeth 161 of the click sleeve 160 providing audible and tactile feedback to the user during dose setting.

As the retaining member 130 is axially connected to the dose insert 120 by its hook element 131 the retaining member 130 is axially moved together with the drive member 150. However, the retaining member 130 cannot rotate during this movement as it is splined to the mechanics holder 30.

FIG. 9*b* depicts the disposable injection pen 3 in a state with a set dose. As shown in FIG. 9*b* the dose sleeve 110, the dose insert 120, the retaining member 130, the click ring 160 and the manual drive member 150 with the dose button 170 are moved in proximal direction relative to the housing 180.

If the user unintentionally sets a dose too large the dose can be corrected by screwing the dose sleeve 110 back into the housing 180. During this reverse rotation the steep flanks of the saw teeth 113 of the dose sleeve 110 abut the steep flanks of the distal saw teeth 161 of the click sleeve 160 and thus rotating the click sleeve 160 together with the dose sleeve 110. As the drive member 150 still does not rotate the proximal saw teeth of the click sleeve 160 ride over the saw teeth 153 of the drive member flange 152 and provide audible and tactile feedback to the user.

During dose setting and dose correction the stop nut 140 is rotated with the dose sleeve as rotationally splined thereto. The stop nut thus moves up or down the thread 154 of the drive member 150, respectively.

As the click sleeve 160 is axially compressed it biases the drive member 150 in proximal direction. That ensures that the distal and proximal saw teeth of the click sleeve 160 are held in engagement or pressed to the saw teeth 113 of the dose sleeve 110 and the saw teeth 153 of the drive member 150.

To dispense a set dose the user pushes the dispensing button 170 in distal direction. As the dispensing button is supported by a central arranged pin inside the drive member 140 any distal movement of the dispensing button 170 is transferred to the drive member 150 and thus it is shifted in the distal direction too.

The shifting of the drive member 150 in distal direction has two effects. Firstly, the click sleeve 160 is further compressed and therefore the radial teeth 155 of the drive member 150 can engage the radial nuts 112 in the dose sleeve 110 thereby rotationally coupling the drive member 150 to the dose sleeve. Secondly, if the drive member 150 is further shifted in distal direction the distal protrusion 151 are moved out of engagement with the nuts 132 and therefore the rotational coupling between the drive member 150 and the retaining member 130 (and the housing) is released.

If the dispensing button is further pushed the dose sleeve 110 starts to rotate back into the housing 180 due to its threaded engagement. The drive member 150 is now rotationally coupled to the dose sleeve 110 and rotates too. As the drive member 150 is in splined engagement with the plunger rod 20 the latter is rotated as well. As the plunger rod 20 is threaded engagement with the mechanics holder thread 31 it is screwed in distal direction. By this distal movement the flange 21 of the plunger rod 20 shifts the piston 6 inside the cartridge 5 in distal direction and thereby causing the medication to be dispensed out of the cartridge 5.

The retaining member 130 is moved distally too (as axially coupled to the dose insert) but does not rotate because it is rotationally fixed relative to the mechanics holder 30 (and the housing). As the drive member 150 keeps its shifted distance relative to the retaining member the protrusions 151 cannot engage the nuts 132 again meaning that the drive member stays rotationally free during dispensing.

As mentioned drive member 150 and the dose sleeve 110 are rotationally coupled and thus there is no relative movement therebetween. The stop nut 140 is thus not moved during dose dispensing.

Figure 10:
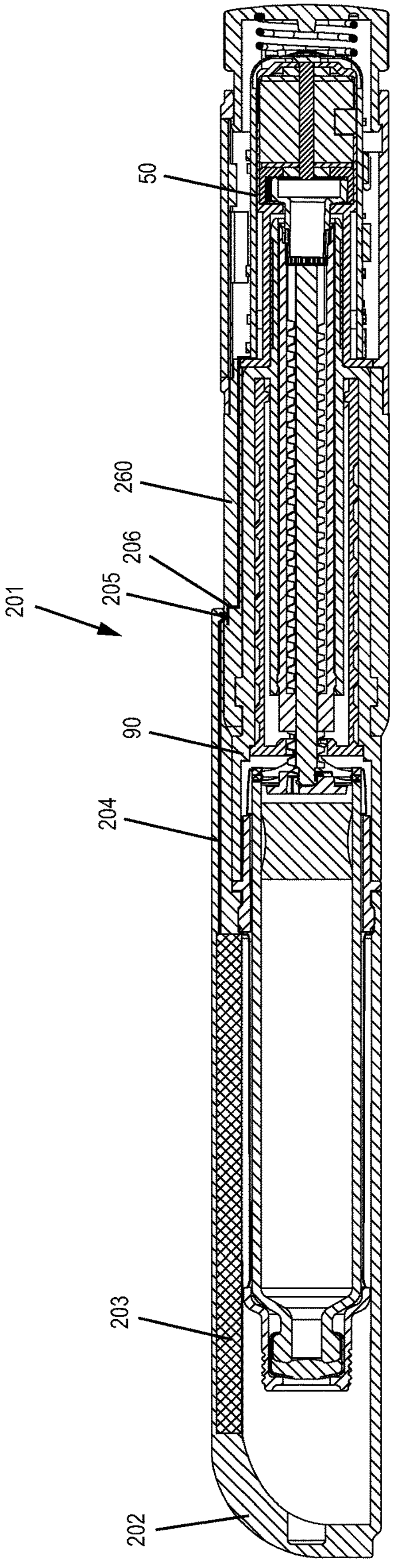
FIG. 10 depicts a sectional view of a semi-disposable pen with a pen cap with a battery.

FIG. 10 shows a sectional view of a further embodiment of the above descripted semi-disposable injection pen 1. The injection pen 201 depicted in FIG. 10 includes a different pen cap 202 and a different display unit than the injection pen 1 descripted above. Namely, the pen cap 202 includes a battery 203 which is electrically connected by a wire 204 inside the cap 202 to a proximal connection element 205.

If the pen cap 203 is attached to the dispensing unit 90 and display unit 260 the connection element 205 mechanically contacts a counter connection element 206 located on an outer surface of the display unit 260. The connection element 206 is electrically connected to the electric circuit of the drive unit 50. If a cap is mounted onto the display unit 260 an electrical connection between the battery 203 in the cap 202 and the battery 54*a*, 54*b* in the drive unit 50 is established. The rechargeable battery 54*a*, 54*b* can thus be charged every time the cap 202 is mounted.

All other components and in particular the dispensing unit 90 and the drive unit 50 of the semi-disposable pen 201 are identical to the components of the injection pen 1. In a further embodiment the cap 202 can also be used with an injection pen 2 with a LEDs. In this case the signaling unit includes an electrical connection element and an electrical connection to the electric circuit of the drive unit as described above.

In the following section the connectivity and the interaction with the user of the semi-disposable injection pens 1, 2 are descripted in detail with respect to FIGS. 10, 12*a* and 12*b*. For the following description the term "semi-disposable injection pen" or "injection pen" is used. The term is to be understood that both types the semi-disposable injection pen with LC-display and the semi-disposable injection pen with LEDs are included.

Figure 11:
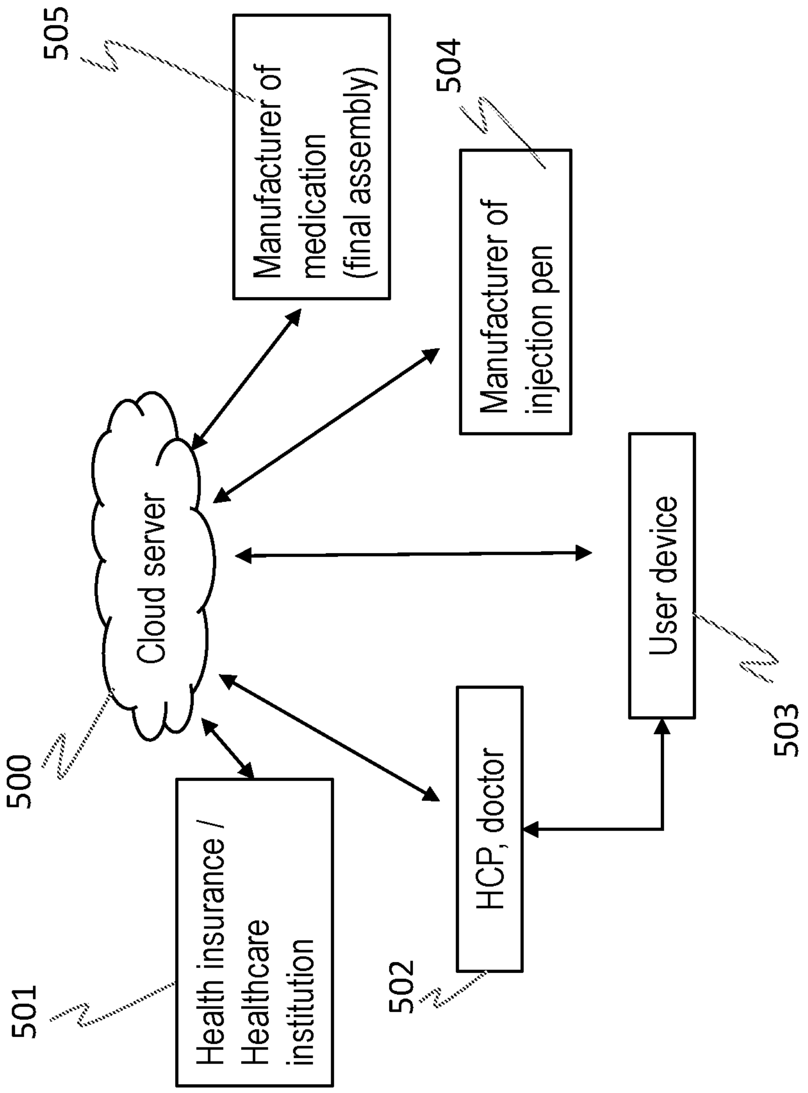
FIG. 11 depicts an overview relating the connectivity.
Figure 12A:
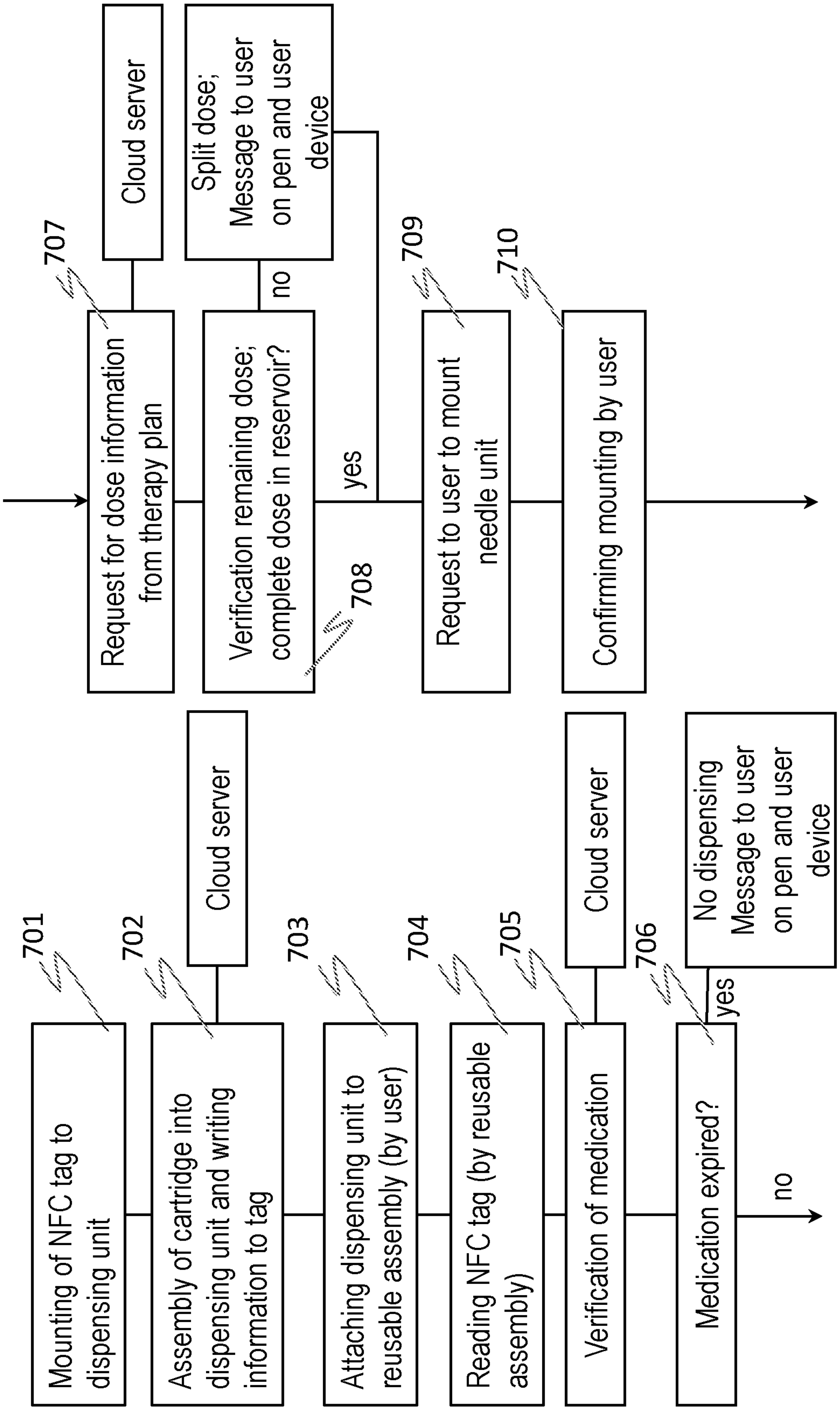
FIGS. 12a, 12b, and 12c depict an example of a flow diagram of the functions of the semi-disposable injection pens.
Figure 12B:
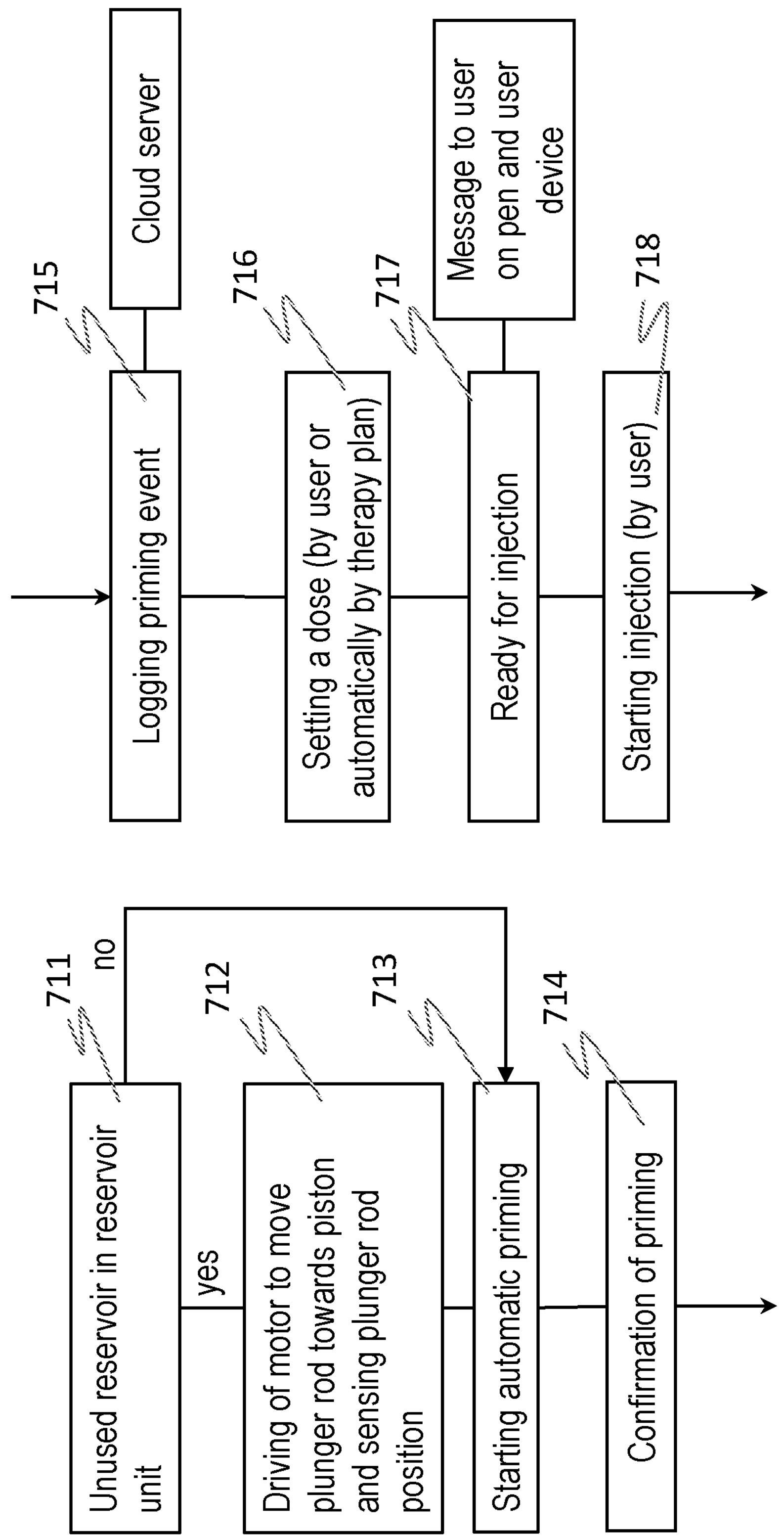

FIG. 11 gives an overview of the connectivity and data transfer with the semi-disposable injections pens 1, 2.

The communication module of the drive unit is wirelessly connected to a user device 503 via Bluetooth or any other short range communication system. The user device 503 is further connected to the internet. The injection pen is previously paired with the user device to allow data transfer.

As stated above with respect to the semi-disposable pen the user device 503 includes a smart phone, a tablet computer, a smart watch, a desktop computer, smart glasses or AR glasses. An application is installed on the user device (for example an "app" running on the smart phone or smart watch) allowing the user to communicate with the injection pen and additionally with the cloud server 500.

Alternatively, the communication module can be connected to a WLAN and via router connected to the internet without using a user device. In further embodiment the communication module includes a mobile module (e. g. sim card) and is directly connected to the internet by a mobile network standard or cellular standard such as GSM, LTE, NR with 5G or 6G. In any case a data communication is established between a cloud server 500 which is connected to the internet and the communication module in the injection pen.

A computer of a healthcare institution 501 (e.g. a healthcare insurance), a computer of a HCP or doctor 502 and a computer of the injection device manufacturer 504 and medication manufacturer 505 is connected to the cloud server 500 by internet as well.

The healthcare institution 501 receives injection data and logged injection events which have been previously sensed and subsequently transmitted to the cloud server 500 by the communication module. The healthcare institution 501 has also access to and can amend a therapy plan stored on the cloud server.

In the same manner the HCP or doctor 502 or medication manufacturer 505 can access the logged injection data and the therapy plan on the cloud server 500. Furthermore, the HCP or medication manufacturer 505 can communicate with the user through messages transmitted between the device of the HCP 502 or the manufacturer respectively and the user device 503 via cloud server 500. The HCP can establish, amend or replace the therapy plan on the cloud server 500. Depending on the setting the controller of the drive unit automatically requests the dose information (and parameters) from the therapy plan. The HCP can thus via cloud server 500 control the administration of the medication.

The user can communicate with the injection pen manufacturer 504 via cloud server 500 in case of a malfunction of the pen or regarding a guarantee claim. The pen manufacturer 504 can send software updates for the drive unit via cloud server 500 and user device 502. Notifications for the user are displayed in this way on the user device 502 and additionally on a display of the injection pen.

In the following section a use case is described with respect to the flow diagram depicted in FIGS. 12*a* and 12*b*.

In a first step 701 the dispensing unit is assembled at the device manufacturer's site and the tag is mounted either on a surface of the interface member or directly on a surface of the cartridge. At step 702 the information as UDI code, medication type and name, expiry date and the volume of cartridge are written to the tag in an only machine-readable format. A unique identifier of each dispensing unit is stored and registered in a database on the cloud server. The unique identifier is linked to instructions or information.

If a user connects a new dispensing unit to the reusable assembly (step 703) by the bayonet connection a sensor of the drive unit detects the replacement or the new dispensing unit and awakes the electronic circuit in the drive unit. The controller activates the tag reader which reads the unique identifier and other tag information from the tag in step 704.

At step 705 the controller of the drive unit processes the read tag information and compares the information with predefined stored information on the cloud server. Optionally, the controller transmits the read unique identifier of the dispensing unit and a unique identifier of the reusable unit together to the cloud server. Accordingly, the set of unique identifiers is stored in a database on the cloud server allowing to record and track the combination of disposable unit and reusable unit used.

Namely, the controller verifies the read medication data with a predefined medication information stored in the storage unit or alternatively transmits the read information to the cloud server. The latter sends a confirmation if the medication corresponds to the correct medication indicated in the therapy plan. If the medication does not match to the therapy plan or to the value in the storage module of the drive unit the controller does not allow starting an injection and displays or signals a warning to the user via LCD or via red LED and additionally sends a message to the user device.

Furthermore, at step 706 the controller compares the read expiry data with the current date to verify whether the medication can be used or whether it already expired. In the latter case the controller informs the user accordingly.

At step 707 the controller communicates via communication module with the cloud server to obtain data of the therapy plan. The server provides the injection information related to the identified medication and the identified user. The controller automatically sets the dose according to the received injection information and subsequently notifies the user about the time and the dose of next upcoming injection.

Alternatively, the injection information received contain only an injection reminder and the user sets the dose manually either directly with the dose knob on the injection device or with the user device which subsequently transmits the set dose to the drive unit.

The controller verifies at step 708 the amount of medication remaining in the cartridge. From the read the controller has the information about the cartridge size. From the encoder the controller obtains the information about already dispensed doses. That means each time the plunger rod is moved for dispensing a dispensing movement is sensed. The controller then determines the dispensed dose and stores the dispensed doses in the storage module. Based on the already dispensed doses of a cartridge and based on a total volume of the cartridge the controller is able to calculate the remaining amount of medication inside a specific cartridge.

The controller allocates all dispensed doses to the corresponding unique identifier and stores the values locally in the storage unit or transmits the values to the cloud server.

This allows the controller to warn the user if a remaining amount of medication is not enough for an upcoming injection. The controller can inform the user that the upcoming injection has to be split (split dose) and that the user has to keep ready a second dispensing unit for the next injection.

At step 709 the controller request a needle to be mounted to the reservoir holder. After the user has confirmed it at step 710 the priming process can start.

At step 711 (FIG. 12*b*) the controller checks whether the plunger rod has to be moved towards the piston inside the cartridge (new, unused dispensing unit) or the plunger rod is in a position ready to prime (already used dispensing unit).

In case the dispensing unit has not been replaced since the last injection the controller starts an automatic priming (step 712), e. g. moves the piston inside the cartridge a very small distance to convey fluid through the needle and to avoid any air bubble in the needle or in the cartridge. In case the dispensing unit has been replaced since the last injection the controller has to move the plunger rod relative to the piston and towards the piston, step 711. For that purpose, the controller firstly uses a fast forward movement and secondly if the flange of the plunger rod is close to the piston the controller drives the plunger rod with a reduced speed until the flange abuts the piston of the cartridge (the information about the volume and therefore the distance to move the plunger rod is contained in the information read from the tag). Subsequently, the controller performs the automatic priming and the user has to confirm the successful termination (drops of medication visible) of the priming at step 714.

Once the priming process is terminated the controller writes a corresponding log in the log book on the cloud server at step 715. Subsequently, the controller sets the planned dose at step 716 or alternatively the user sets the dose according to dose information received from the cloud server (see previous step 707).

The controller further confirms the user that the planned dose is now ready to be administered (step 717). The user then can start the injection at step 718 by pushing the dispensing button or dose knob, respectively.

Figure 12C:
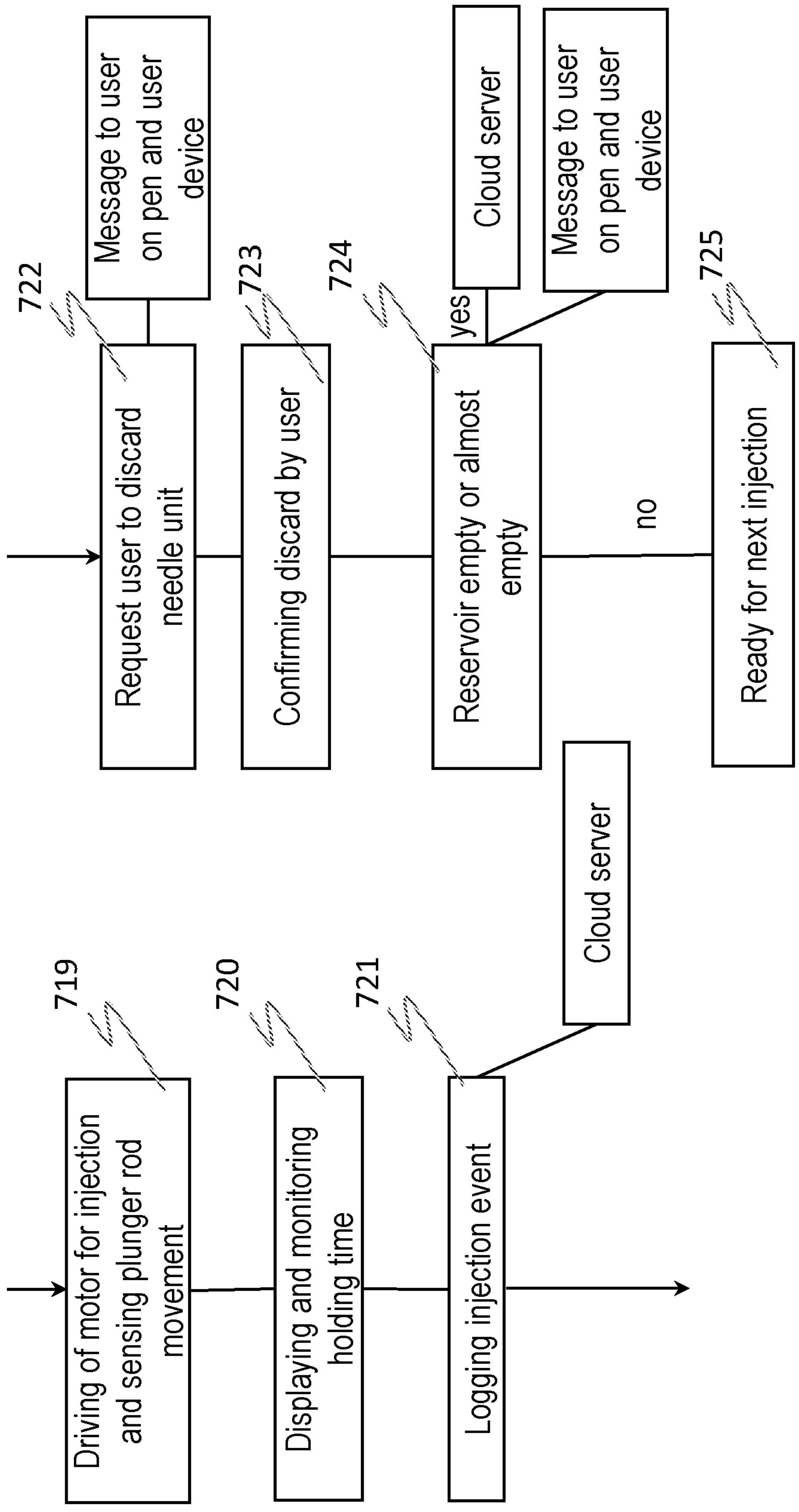

At step 719 (FIG. 12*c*) the controller controls the drive unit to move the plunger rod in a distal direction to dispense the dose. The encoder in the drive unit measures the movement of the drive member and the controller determines the actually dispensed units based on the measurement. The measured values are stored as a log record in the storage module together with the time and the information about the medication (below step 721). All logged events are also transmitted to the cloud server. The controller updates the stored data about the remaining medication in the cartridge accordingly.

After the set dose has been injected the controller signals the user to keep the injection pen onto the injection site for a predefined time (holding time) at step 720. For that purpose, the controller decrements a value of the predefined period displayed on the LCD or the controller activates a LED during the holding time. The holding time is additionally displayed on the user device. The holding time depends on the medication. The controller receives the information about a specific holding time when reading the tag of the dispensing unit. Furthermore, the controller monitors (by inertial sensors) that the user keeps holding the injection pen onto the injection site during the holding time. In case the user does not respect the holding time the controller indicates a warning and optionally updates the log entry. Upon expiry of the holding time the controller sends the acquired injection data to the cloud server at step 721.

At step 722 after the injection has been completed the controller signals the user that the needle has to be discarded. Such information is displayed on the LCD of the display unit or by different LEDs of the signaling unit respectively and on the user device. The user has to confirm the disposal at step 723.

In case the cartridge is almost empty the controller warns the user or displays a request for replacing the dispensing unit at step 724. As described above the controller informs the user in case the next injection has to be split (split dose). Subsequently, at step 725 the controller signals that the device is ready for the next injection.

In an alternative embodiment the descripted transmission and storage of data on the cloud server is provided by the storage module or the communication module respectively of the drive unit itself. That means the therapy plan, the predefined doses, injection instruction, user specific alerts and the like are stored in the storage module on the injection device. The controller reads the information from the storage module, for example, if a new dispensing unit is attached to the drive unit. Consequently, there is no need for a data connection to any external device (user device or cloud server) and the above descripted function are still available. That may be advantageous in particular if there is no internet connection available or if injection data are confidential or if injection data are not supposed to be transmitted via data network.

In a further embodiment the drive unit is directly paired and connected to the cloud server. As mentioned above in connection with FIG. 11 the communication module includes in this case a wireless module adapted to transmit data directly to the cloud server. That means the controller communicates directly with the cloud server and can obtain the injection information and therapy plan directly from the cloud. Thus, there is no need to pair and connect the injection pen to a user device. All function descripted above are maintained by the direct data transfer between the communication module of the drive unit and the cloud server.

In this case, the doctor, the HCP, the manufacturer of the injection pen or the manufacturer of the medication connects the drive unit to the cloud server before the device is delivered to the user. That is advantageous as the user does not have to pair and connect the drive unit with a local network or with the user device. Additionally or instead the drive unit is paired to the user device at the manufacturer's site if the user data are known at that time.

In a further embodiment drive unit is paired with a blood sugar measurement (BGM) device or with a continuous blood sugar measurement (CGM) device and is adapted to receive values of these devices. In this embodiment the controller determines the dose to be administered based on received BGM or CBM values. Additionally or instead, the controller can receive the values from the therapy plan or instructions from a HCP stored on the cloud server. If necessary, the user can manually adjust or correct the dose to be administered by the dose knob at the drive unit. This is useful, for example, for a diabetes therapy requiring the user to adjust a set dose of insulin or insulin derivatives depending on the meal or on other circumstances.

The automatic drive unit 50 and the display unit 60 (injection pen 1) or the drive unit 50 and the signaling unit 80 (injection pen 2) are assembled at the manufacturer's site and cannot be separated by the user of the injection device. However, in a preferred embodiment the drive unit 50 and display unit 60 or the signaling unit 80 are connected to each other by a snap lock, by a thread or by any other form-locked connection which can be released by the manufacturer, by a repair facility or by any trained and authorized technician but not by the user.

This allows to separate the components or units of the injection device 1, 2 upon the device 1, 2 has reached its end of life or if the device has been returned to the supplier. Some or all components or units of the used injection device 1, 2 may be reused for another injection device in order to reduce waste and energy consumption (circular economy). Accordingly, the used parts or units, in particular the drive unit 50, the display unit 60 or the signaling unit 80 can be used for more than one product cycle.

While the disclosure has been described in detail in the drawings and foregoing description, such description is to be considered illustrative or exemplary and not restrictive. Variations to the disclosed embodiments can be understood and effected by those skilled in the art and practising the claimed invention, from a study of the drawings, the disclosure, and the appended claims. In the claims, the word "including" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

| | |
|---|---|
| 1 | Semi-disposable pen with LCD |
| 2 | Semi-disposable pen with LEDs |
| 3 | Fully disposable pen |
| 5 | Cartridge |
| 6 | Piston |
| 7 | Pen cap |
| 10 | Cartridge holder |
| 20 | Plunger rod |
| 21 | Flange |
| 30 | Mechanics holder |
| 31 | Thread |
| 32a,b | Elastic elements |
| 33 | Thread element |
| 40 | Reservoir unit |
| 50 | Automatic drive unit |
| 51a,b | Support structure |
| 51b | Support structure |
| 52 | Automatic drive member |
| 53 | Electric motor |
| 54a,b | Battery |
| 55 | PCB |
| 56 | Communication module |
| 57 | Storage module |
| 58 | Motor shaft |
| 59 | distal teeth |
| 60 | Display unit |
| 61 | Distal housing |
| 62 | Proximal housing |
| 63 | Spring |
| 64 | Dose knob |
| 65 | LCD |
| 70 | Interface member |
| 71 | Plunger rod driver |
| 72 | Housing |
| 73 | Teeth |
| 74 | Protrusion |
| 75 | label with tag |
| 76 | tag |
| 80 | Signaling unit |
| 81 | Distal housing |
| 82 | Proximal housing |
| 84 | Dispensing button |
| 85a,b,c | LEDs |
| 90 | Dispensing unit |
| 100 | Manual drive unit |
| 110 | Dose sleeve |
| 111 | Grip portion |
| 112 | Nuts |
| 113 | Saw teeth |
| 114 | Radial nuts |
| 120 | Dose insert |
| 121 | Nut |
| 130 | Retaining member |
| 131 | Hook element |
| 132 | Nuts |
| 140 | Stop nut |
| 150 | Manual drive member |
| 151 | Protrusion |
| 152 | Flange |
| 153 | Saw teeth |
| 154 | Thread |
| 155 | Radial teeth |
| 160 | Click sleeve |
| 161 | Saw teeth |
| 170 | Dispensing button |

-continued

| | |
|---|---|
| 171 | Rib |
| 180 | Housing |
| 201 | Injection Pen |
| 202 | Cap |
| 203 | Battery |
| 204 | Wire |
| 205 | Connection element |
| 206 | Connection element |
| 260 | Display unit |

What is claimed is:

1. A modular injection system, comprising:

a first injection device, comprising:

a first reservoir unit comprising a reservoir filled with medication, a housing for holding the reservoir and a plunger rod adapted to advance a piston inside the reservoir to dispense the medication;

a first automatic drive unit releasably attachable to the first reservoir unit and comprising an automatic drive member automatically driven by a power source and adapted to be releasably coupled to the plunger rod; and an interface member adapted to be coupled to the housing and comprising a plunger rod driver adapted to be coupled to the plunger rod of the first injection device, wherein the plunger rod driver comprises a coupling element adapted to releasably couple the plunger rod driver to the automatic drive member and a second injection device, comprising:

a second reservoir unit; and a manual drive unit coupled to the second reservoir unit and comprising a manual drive member manually driven and coupled to a plunger rod of the second reservoir unit, wherein the first reservoir unit and the second reservoir unit are identical.

2. The modular injection system according to claim 1, wherein the first injection device further comprises a signaling unit coupled to the first automatic drive unit and comprising a light signaling means for signaling an injection status of the first injection device.

3. The modular injection system according to claim 2, wherein the injection system further comprises a third injection device comprising:

a third reservoir unit;

a second automatic drive unit; and a display unit coupled to the second automatic drive unit and comprising a display adapted for alphanumerically displaying an injection status of the third injection device, wherein the first reservoir unit and the third reservoir unit are identical, and the first automatic drive unit and the second automatic drive unit are identical.

4. The modular injection system according to claim 3, wherein the first injection device comprises a dose setting member coupled to the first automatic drive unit for manually setting or correcting a dose.

5. The modular injection system according to claim 1, wherein the automatic drive member comprises an electric motor, and wherein the first automatic drive unit further comprises a controller and a communication module, wherein the controller is adapted to control the electric motor based on injection information received via the communication module.

6. The modular injection system according to claim 1, wherein the first automatic drive unit further comprises injection status sensing means for monitoring an injection status, and storage means for storing acquired injection status information.

7. The modular injection system according to claim 6, wherein at least the first reservoir unit or the second reservoir unit comprises a machine-readable tag with identification information on the medication inside the reservoir or uniquely identifying the reservoir unit, and wherein the first automatic drive unit comprises a tag reader adapted to read the identification information of the machine-readable tag.

8. The modular injection system according to claim 7, wherein based on the identification information of the machine-readable tag, the first automatic drive unit is adapted to control an electric motor of the automatic drive member or to output a notification to a user.

9. The modular injection system according to claim 7, wherein the first automatic drive unit is adapted to determine an amount of dispensed medication or an amount of the medication remaining inside the reservoir based on the acquired injection status information, and is adapted to assign the amount to the read identification information of the corresponding reservoir unit.

10. The modular injection system according to claim 9, wherein the first automatic drive unit is adapted to signal that the amount of dispensed medication or the amount of medication remaining inside the reservoir of the first reservoir unit exceeds a predefined threshold.

11. The modular injection system according to claim 1, wherein at least the first reservoir unit or the second reservoir unit comprises a machine-readable tag with identification information on the medication inside the reservoir or uniquely identifying the reservoir unit, and wherein the first automatic drive unit comprises a tag reader adapted to read the identification information of the machine-readable tag.

12. The modular injection system according to claim 11, wherein based on the identification information of the machine-readable tag, the first automatic drive unit is adapted to control an electric motor of the automatic drive member or to output a notification to a user.

13. A modular injection system, comprising:

a first injection device, comprising:

a first reservoir unit comprising a reservoir filled with medication, a housing for holding the reservoir and a plunger rod adapted to advance a piston inside the reservoir to dispense the medication; and a first automatic drive unit releasably attachable to the first reservoir unit and comprising an automatic drive member automatically driven by a power source and adapted to be releasably coupled to the plunger rod; and a second injection device, comprising:

a second reservoir unit; and a manual drive unit coupled to the second reservoir unit and comprising a manual drive member manually driven and coupled to a plunger rod of the second reservoir unit, wherein the first reservoir unit and the second reservoir unit are identical, wherein the manual drive unit further comprises a dose setting member, a housing, and a retaining member with an engaging element, wherein during dose setting, the manual drive member can be moved in a longitudinal direction relative to the manual drive unit housing, and the manual drive member can be held by the engaging element in a rotationally fixed manner relative to the manual drive unit housing, and wherein during dose dispensing, the manual drive member is released from the engaging element and can rotate relative to the manual drive unit housing.

14. The modular injection system according to claim 13, wherein the first injection device further comprises a signaling unit coupled to the first automatic drive unit and comprising a light signaling means for signaling an injection status of the first injection device.

15. The modular injection system according to claim 13, wherein at least the first reservoir unit or the second reservoir unit comprises a machine-readable tag with identification information on the medication inside the reservoir or uniquely identifying the reservoir unit, and wherein the first automatic drive unit comprises a tag reader adapted to read the identification information of the machine-readable tag.

16. The modular injection system according to claim 13, wherein the automatic drive member comprises an electric motor, and wherein the first automatic drive unit further comprises a controller and a communication module, wherein the controller is adapted to control the electric motor based on injection information received via the communication module.

17. The modular injection system according to claim 13, wherein the first automatic drive unit further comprises injection status sensing means for monitoring an injection status, and storage means for storing acquired injection status information.

18. A modular injection system, comprising:

a first injection device, comprising:

a first reservoir unit comprising a reservoir filled with medication, a housing for holding the reservoir and a plunger rod adapted to advance a piston inside the reservoir to dispense the medication; and a first automatic drive unit releasably attachable to the first reservoir unit and comprising an automatic drive member automatically driven by a power source and adapted to be releasably coupled to the plunger rod; and a second injection device, comprising:

a second reservoir unit; and a manual drive unit coupled to the second reservoir unit and comprising a manual drive member manually driven and coupled to a plunger rod of the second reservoir unit, wherein the first reservoir unit and the second reservoir unit are identical, wherein at least the first reservoir unit or the second reservoir unit comprises a machine-readable tag with identification information on the medication inside the reservoir or uniquely identifying the reservoir unit, and wherein the first automatic drive unit comprises a tag reader adapted to read the identification information of the machine-readable tag, and wherein the first automatic drive unit comprises a unique identifier, and wherein the first automatic drive unit is adapted to transmit an identifier set comprising the unique identifier and the identification information to a database.

* * * * *